United States Patent [19]

Maywald et al.

[11] Patent Number: 5,378,680
[45] Date of Patent: Jan. 3, 1995

[54] DICARBOXIMIDES AND THEIR USE AS HERBICIDES

[75] Inventors: Volker Maywald, Ludwigshafen; Klaus Ditrich, Bad Duerkheim; Thomas Kuekenhoehner, Frankenthal; Gerhard Hamprecht, Weinheim; Wolfgang Feund, Neustadt; Karl-Otto Westphalen, Speyer; Matthias Gerber, Mutterstadt; Helmut Walter, Obrigheim, all of Germany

[73] Assignee: BASF Aktiengesellschaft, Ludwigshafen, Germany

[21] Appl. No.: 931,951

[22] Filed: Aug. 19, 1992

Related U.S. Application Data

[62] Division of Ser. No. 718,639, Jun. 21, 1991, Pat. No. 5,176,739.

[30] Foreign Application Priority Data

Jun. 23, 1990 [DE] Germany ............... 4020072
Jul. 16, 1990 [DE] Germany ............... 4022566

[51] Int. Cl.$^6$ ................ A01N 43/76; C07D 498/04
[52] U.S. Cl. .................... 504/270; 504/271; 504/267; 504/269; 504/263; 546/101; 548/159; 548/207; 548/218; 548/242; 548/136
[58] Field of Search ............. 504/270, 271; 548/218, 548/242

[56] References Cited

U.S. PATENT DOCUMENTS

| 4,681,949 | 7/1987 | Brunelle ............... 548/461 |
| 4,785,116 | 11/1988 | Eilingsfeld et al. ....... 548/212 |
| 5,053,508 | 10/1991 | Schichser et al. ........ 544/357 |

FOREIGN PATENT DOCUMENTS 0337263 10/1989 European Pat. Off.

OTHER PUBLICATIONS

Journal of Heterocyclic Chemistry, Jul.-Aug., 1989, vol. 26, No. 4, pp. 885-892, A. R. Katritzky, et al., "Novel Chromophoric Heterocycles Based on Maleimide and Naphthoquinone".

Synthesis, 1988, pp. 449-452, Jun. 1988, Karl-Heinz Etzback, et al., "Synthese Van 5-Ring-Heterocyclen Aus Maleinimiden".

Journal of Heterocyclic Chemistry, vol. 25, No. 1, Jan.-Feb., 1988, pp. 901-906, A. R. Katritzky, et al., "Some Novel Quinone-Type Dyes Containing Naphthoquinone and Related Fused Ring Systems", May-Jun. 1988.

J. Chem. Soc. Perkin Trans., 1, 1981, pp. 2692-2694, K. T. Potts, et al., "Reaction of Dehydrodithizone with Benzyne and Diphenyl-Cyclopropenethione. Isolation of N-(1,2-Diphenyldiazonia)-1,3-Benzothiazole-2-Aminate and the Formation of 2--Phenylazo-4,6,7 . . . ".

J. Chem. Soc. Perkin Trans. 1, 1982, pp. 2391-2394, A. Camparini, et al., "Syntheses and Reactivities of 3-Methylisoxazolo[4,5-b]Pyridines".

Arch. Pharm., 320, 1987, pp. 1281-1283, S. S. Ghabrial, "Reaction with Maleimides V$^1$): Synthesis of New Pyrrolo[3,4-d]-Isoxazole Derivatives".

Shimizu, T. et al. *Bull. Chem. Soc. Jpn,* 57, 2531-2534 (1984).

Primary Examiner—Mary C. Lee
Assistant Examiner—Jacqueline Haley
Attorney, Agent, or Firm—Oblon, Spivak, McClelland, Maier & Neustadt

[57] ABSTRACT

Dicarboximides of the formulae Ia, Ib and Ic

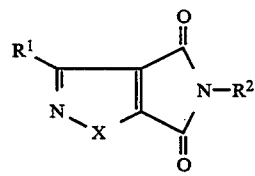

Ia

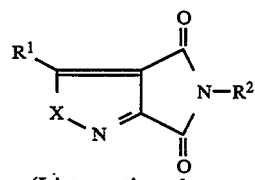

Ib (List continued on next page.)

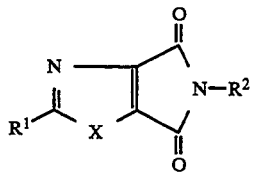

where
X is oxygen or sulfur,
$R^1$ is hydrogen, halogen, cyano, alkyl, cycloalkyl, alkenyl, alkynyl, alkoxy, alkenyloxy, alkynyloxy, alkylthio, haloalkoxy, haloalkylthio, alkylsulfonyl, haloalkylsulfonyl, phenyl, phenylalkyl, phenoxy or phenylthio, a 5-membered or 6-membered saturated or aromatic heterocyclic radical containing one or two hetero atoms selected from the group consisting of oxygen, sulfur and nitrogen, where the stated organic radicals may be further substituted, and
$R^2$ is hydrogen, hydroxyl, alkoxy, alkyl, cycloalkyl, alkenyl, alkynyl, di-$C_1$–$C_4$- alkylamino, a 5-membered or 6-membered heterocyclic saturated or aromatic radical having one or two hetero atoms selected from the group consisting of oxygen, sulfur and nitrogen, phenyl or naphthyl, where the stated organic radicals may be further substituted,
and plant-tolerated salts of the dicarboximides I, except for 3-methylisoxazole-4,5-dicarboximide and thiazole-4,5-dicarboximides in which $R^2$ is phenyl when $R^1$ is methyl or 2-thiazolyl,
and herbicides containing these compounds.

26 Claims, No Drawings

DICARBOXIMIDES AND THEIR USE AS HERBICIDES

This is a division of application Ser. No. 07/718,639, filed on Jun. 21, 1991, now U.S. Pat. No. 5,176,739.

Dicarboximides

The present invention relates to dicarboximides of the formulae Ia, Ib and Ic

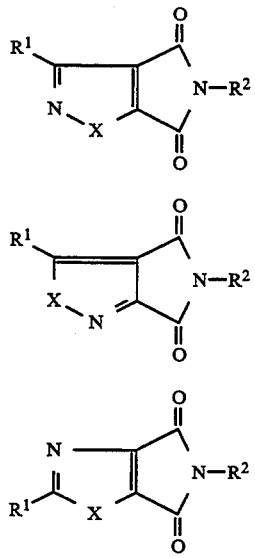

where

X is oxygen or sulfur, $R^1$ is hydrogen, halogen, cyano, $C_1-C_6$-alkyl which may carry from one to five halogen atoms and/or one or two of the following radicals: $C_3-C_6$-cycloalkyl, $C_1-C_4$-alkoxy, $C_1-C_4$-haloalkoxy, $C_1$-alkylthio, $C_1-C_4$-haloalkylthio, $C_1-C_4$-alkylsulfonyl, $C_1$-haloalkylsulfonyl or cyano, $C_3-C_8$-cycloalkyl which may carry from one to three of the following radicals: $C_1-C_4$-alkyl or halogen, $C_2-C_6$-alkenyl which may carry from one to three of the following radicals: halogen, $C_1-C_3$-alkoxy and/or a phenyl radical which in turn may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, $C_2-C_6$-alkynyl which may carry from one to three of the following radicals: halogen, $C_1-C_3$-alkoxy and/or a phenyl radical which in turn may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, $C_1-C_4$-alkoxy, $C_2-C_6$-alkenyloxy, $C_2-C_6$-alkynyloxy, $C_1-C_4$-alkylthio, $C_1-C_4$-haloalkoxy, $C_1-C_4$-haloalkylthio, $C_1-C_4$-alkylsulfonyl or $C_1-C_4$-haloalkylsulfonyl, phenoxy or phenylthio which may carry from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, a 5-membered or 6-membered saturated or aromatic heterocyclic radical containing one or two hetero atoms selected from the group consisting of oxygen, sulfur and nitrogen, where the ring may carry one or two of the following radicals: $C_1-C_3$-alkyl, halogen, $C_1-C_3$-alkoxy or $C_1-C_3$-alkoxycarbonyl, a fused aromatic radical selected from the group consisting of benzofuran-2-yl, benzofuran-3-yl, isobenzofuran-2-yl, benzothiophen-2-yl, benzothiophen-3-yl, isobenzothiophen-2-yl, indol-2-yl, indol-3-yl, 1,2-benzoisoxal-3-yl, benzoxazol-2-yl, 1,2-benzoisothiazol-3-yl, benzothiazol-2-yl, indazol-3-yl, (1H)-benzimidazol-2-yl, quinol-3-yl, quinol-5-yl, quinol-6-yl, quinol-8-yl, isoquinol-1-yl and isoquinol-5-yl, where this radical may carry one or two of the following radicals: alkyl as stated above, in particular methyl, halogen as stated above, in particular fluorine or chlorine, alkoxy as stated above, in particular methoxy or ethoxy, or alkoxycarbonyl, such as methoxycarbonyl or ethoxycarbonyl, in particular methoxycarbonyl, phenyl or phenyl-$C_1-C_4$-alkyl where the phenyl nucleus in each case is unsubstituted or substituted by from one to three of the following groups: $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, halogen, nitro or cyano, $R^2$ is hydrogen, hydroxyl, $C_1-C_4$-alkoxy, $C_1-C_6$-alkyl which may carry from one to three of the following groups: cyano, $C_1-C_4$-alkoxy-$C_1-C_4$-alkoxy, $C_1-C_4$-alkoxy, $C_1-C_4$-haloalkoxy, $C_1-C_4$-alkylthio, $C_1-C_4$-haloalkylthio, di-$C_1-C_4$-alkylamino, halogen, $C_3-C_8$-cycloalkyl or phenyl, where the phenyl ring in turn may carry from one to three of the following radicals: halogen, cyano, nitro, $C_1-C_4$-alkyl, $C_1-C_4$-haloalkyl, $C_1-C_4$-alkoxy, $C_1-C_4$-haloalkoxy, $C_1-C_4$-alkylthio or $C_1-C_4$-haloalkylthio, $C_3-C_8$-cycloalkyl which may carry from one to three of the following groups: $C_1-C_6$-alkyl, $C_1-C_6$-haloalkyl, $C_1-C_4$-alkoxy, $C_1-C_4$-haloalkoxy, halogen, nitro or cyano, $C_3-C_6$-alkenyl which may be monosubstituted to trisubstituted by halogen and/or monosubstituted by phenyl, where the phenyl radical in turn may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano, or nitro, $C_3-C_6$-alkynyl which may be monosubstituted to trisubstituted by halogen and/or monosubstituted by phenyl, where the phenyl radical in turn may carry from one to three of the following groups: $C_1-C_4$-alkyl, $C_1-C_4$-haloalkyl, $C_1-C_4$-alkoxy, $C_1-C_4$-haloalkoxy, $C_1-C_4$-alkylthio, $C_1-C_4$-haloalkylthio, halogen, cyano or nitro, di-$C_1-C_4$-alkylamino, a 5-membered or 6-membered heterocyclic saturated or aromatic radical which has one or two hetero atoms selected from the group consisting of oxygen, sulfur and nitrogen and which may be monosubstituted to trisubstituted by $C_1-C_4$-alkyl or halogen, a fused aromatic radical selected from the group consisting of benzofuran-2-yl, benzofuran-3-yl, isobenzofuran-2-yl, benzothiophen-2-yl, benzothiophen-3-yl, isobenzothiophen-2-yl, indol-2yl, indol-3yl, 1,2-benzoisoxal-3-yl, benzoxazol-2-yl, 1,2-benzoisothiazol-3-yl, benzothiazol-2yl, indazol-3yl, (1H)-benzimidazol-2-yl, quinol-3yl, quinol-5-yl, quinol-6-yl, quinol-8-yl, isoquinol-1-yl and isoquinol-5-yl, where this radical may be monosubstituted to trisubstituted by $C_1$-$C_4$-alkyl or halogen, phenyl which may carry from one to four of the following groups: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro, cyano, formyl, phenyl, $C_1$-$C_4$-alkanoyl, $C_1$-$C_4$-haloalkanoyl or $C_1$-$C_4$-alkoxycarbonyl, naphthyl which may be monosubstituted to trisubstituted by $C_1$-$C_4$-alkyl or halogen, and plant-tolerated salts of the dicarboximides, except for 3-methylisoxazole-4,5-dicarboximide and thiazole-4,5-dicarboximides in which $R^2$ is phenyl when $R^1$ is methyl or 2-thiazolyl.

The present invention furthermore relates to processes for the preparation of these compounds and herbicides which contain one or more compounds Ia, Ib or Ic in which the substituents have the abovementioned meanings, including 3-methylisoxazole-4,5-dicarboximide and thiazole-4,5-dicarboximides in which $R^2$ is phenyl when $R^1$ is methyl or 2-thiazolyl.

Arch. Pharm. 320 (1987), 1281–1283 discloses isoxazoledicarboximides which are ethoxycarbonylmethyl-substituted in the 3-position. Furthermore, J. Chem. Soc. Perkin Trans. 1 (1982), 2391–2394 describes 3-methylisoxazole-4,5-dicarboximide. Synthesis 1988, 449–452 describes 5-amino-substituted isothiazoledicarboximides as intermediates for the preparation of dyes.

Specifically substituted thiazole-4,5-dicarboximides are disclosed in J. Het. Chem. 26 (1989), 885, Synthesis 1988, 449, J. Het. Chem. 25 (1988), 901 and J. Chem. Soc. Perkin Trans. 1 (1981), 2692), but the prior art cited gives no indication of the herbicidal properties of the dicarboximides.

It is an object of the present invention to provide novel herbicidal compounds.

We have found that this object is achieved and that the dicarboximides Ia, Ib and Ic defined at the outset have herbicidal properties.

The novel dicarboximides I can be prepared in various ways; they are obtained, for example, by the following processes:

Route A

By removal of water using water-eliminating agents, for example acetic anhydride, inorganic acid halides, such as thionyl chloride, phosphorus(III) or phosphorus(V) halides, such as phosphorus trichloride or phosphorus pentachloride, phosgene, p-toluenesulfonyl chloride or propanephosphonic anhydride, the compounds IIa and IIb are converted into the dicarboximides of the formula I.

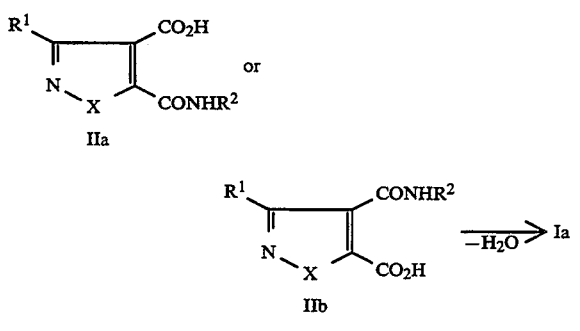

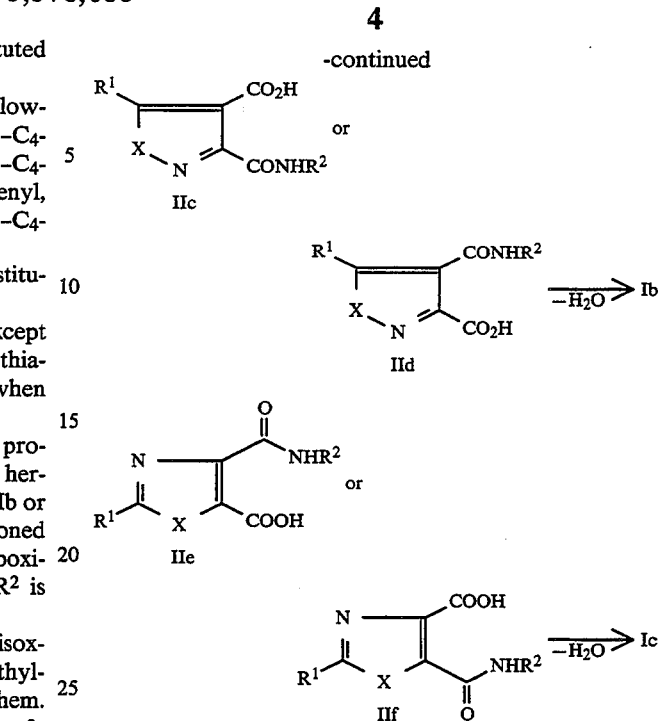

The reaction is advantageously carried out by a procedure in which the carboxamides in an inert organic solvent are initially taken and about a molar amount of a water-eliminating agent, if necessary likewise dissolved in an inert solvent, is added dropwise. The mixture can be worked up in a conventional manner, for example by hydrolysis with water and filtration under suction or extraction of the produce with an organic solvent and evaporation of the organic solvent.

Solvents advantageously used for these reactions are halohydrocarbons, e.g. tetrachloroethane, methylene chloride, chloroform, dichloroethane, chlorobenzene and 1,2-dichlorobenzene, ethers, e.g. diethyl ether, methyl tert-butyl ether, dimethoxyethane, diethylene glycol diethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one, aromatics, e.g. benzene, toluene, xylene, pyridine and quinoline, ketones, e.g. acetone or methyl ethyl ketone, or corresponding mixtures.

The dehydration reaction can be carried out at from $-10°$ C. to the reflux temperature of the particular solvent, preferably from $0°$ to $150°$ C.

The molar ratios in which the required starting compounds are reacted with one another are in general from 0.9:1 to 5:1 for the ratio of water-eliminating agent to amide.

The concentration of the educts in the solvent (mixture) is in general from 0.1 to 5, preferably from 0.2 to 2, mol/l.

The preparation of the dicarboxylic acid monoamides IIa which are required as starting materials for this process is described in DE-A-38 12 225.

The dicarboxylic acid monoamides IIc can be obtained as described in DE-A 39 31 627. Starting materials are isoxazole- and isothiazole-3-carbonyl halides VII, which are reacted with an amine VIII. Preferred carbonyl halides VII are the chlorides. In an advantageous procedure, the carbonyl halide in an inert organic solvent such as dichloromethane, or in an ether, such as diethyl ether or methyl tert-butyl ether, is reacted with an amine VIII, likewise dissolved in an organic solvent. The amine VIII is advantageously used in from 2 to 5, preferably from 2 to 3, times the molar amount in order to bind the resulting hydrogen halide. The reaction can also be carried out in the presence of an auxiliary base, for example a tertiary amine (triethylamine). In this case, from 1 to 1.5 mole equivalents of amine VIII are sufficient. The reaction temperature may be from 0° to 50° C., preferably from 0° to 20° C. The reaction is generally complete after from 1 to 12 hours. The mixture can be worked up in a conventional manner, for example by hydrolysis with water and extraction of the product IX with an organic solvent and evaporation of the organic solvent.

The 3-aminocarbonylisoxazole-4-carboxylic acids or 3-aminocarbonylisothiazole-4-carboxylic acids of the formula IIc are obtained from the isoxazol- or isothiazolamides IX by reaction with an alkyllithium, such as n-butyllithium, sec-butyllithium or methyllithium, preferably with the addition of a solvent which is inert under the reaction conditions, such as diethyl ether or tetrahydrofuran. As a rule, this reaction is carried out under an inert gas atmosphere, for example a nitrogen atmosphere, at from −70° to −80° C. In this process, the alkyllithium compound is generally used in 2–3 times the molar amount, based on the amide of the formula IX used. After complete reaction, the mixture is treated with carbon dioxide, preferably in an inert solvent, such as diethyl ether or, for example, tetrahydrofuran, the desired products of the formula IIc being obtained.

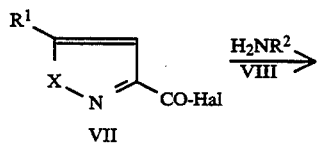

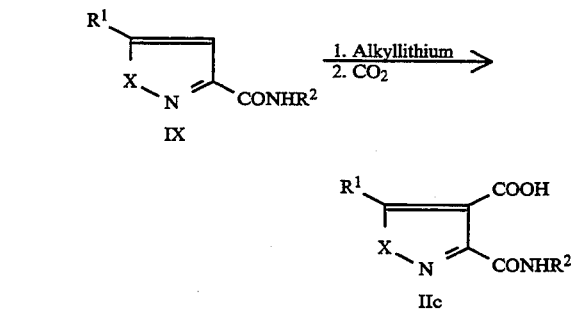

Hal=halogen, such as Cl or Br

The isoxazole- and isothiazole-3-carbonyl halides VII required as the starting material for this process are known from the literature or can be prepared in a conventional manner from the corresponding carboxylic acids.

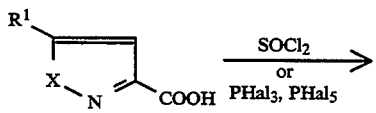

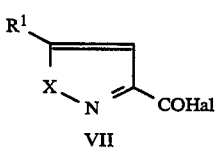

The carboxylic acids required for this process are know from the literature (Beilstein, main volume and 1st–5th supplements, volume 27; R. W. Wiley, The Chemistry of Heterocylic Compounds, Five- and Six-Membered Compounds with Nitrogen and Oxygen, Interscience Publishers, New York, London (1962)) or can be prepared by methods generally known from the literature, for example by oxidation of the corresponding alcohols or aldehydes or by hydrolysis of the corresponding nitriles.

The dicarboxylic acid monoamides IIe and IIf used as starting materials can be obtained by various processes:
a) by hydrolyzing the corresponding alkyl esters, such as methyl or ethyl esters, in accordance with the conditions indicated under Reaction step A.

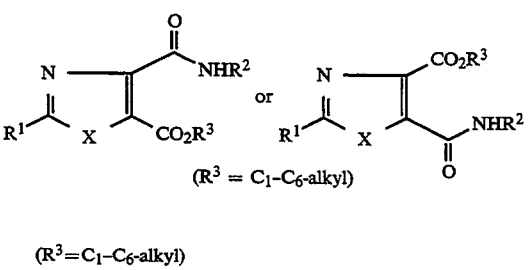

($R^3 = C_1$–$C_6$-alkyl)

These alkyl esters are obtained by a method in which a diester of the formula III is hydrolyzed in a conventional manner with one equivalent of an aqueous base to give the monoesters IVa and IVb, and the latter are then first converted, separately or as a mixture, into the halide or another activated form of the carboxylic acid, and these derivatives are then amidated with an amine VIII.

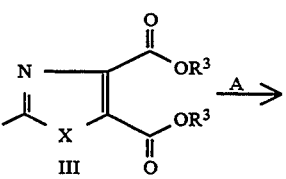

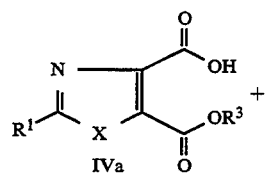

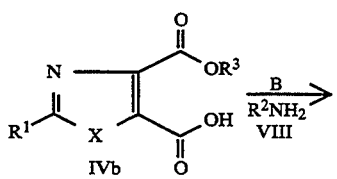

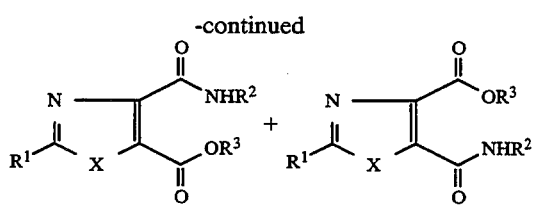

The individual reaction steps A and B of the synthesis sequence can be carried out as follows:

Reaction step A:

The partial hydrolysis of the diester III to give the monoesters IVa and IVb is usually carried out at from −20° to 60° C., preferably from −10° to 30° C., in an inert, water-miscible organic solvent in the presence of from 1.0 to 1.2 mol equivalents of a base.

Particularly suitable bases are hydroxides of alkali metal cations, such as sodium hydroxide or potassium hydroxide. The base is generally added as a 5-20% strength aqueous solution.

Preferred solvents for this reaction are, for example, dioxane or the alcohol corresponding to the ester component in the formula III.

The reaction mixture is usually worked up by acidifying it, the desired product separating out as a solid or as an oil. Isolation is effected in a conventional manner by filtration or extraction.

The mixture of the two isomers IVa and IVb can be separated by fractional crystallization or by chromatographic methods, or it can be further reacted without separation.

Reaction step B:

The monoesters Iva and IVb are first converted in a conventional manner into the halide or another activated form of the carboxylic acid function and then these derivatives are amidated with an amine VIII.

Other activated forms of the carboxylic acid in addition to halides, in particular the chlorides or bromides, are, for example, imidazolides. The halides are generally preferred.

They are obtained by reaction the carboxylic acids IVa and IVb with a halogenating agent, such as thionyl chloride, thionyl bromide, phosphorus oxychloride or -bromide, phosphourus tri- and pentachloride or -bromide, phosgene and elemental chlorine and bromine. The halogenating agent is used in an amount of from 1 to 5, preferably from 1 to 2, mol equivalents.

The reaction takes place at from 0° C. to the boiling point of the halogenating agent or, if it is carried out in the presence of an inert organic solvent, at the boiling point of the latter, preferably at from 20° to 120° C.

Examples of suitable solvents are hydrocarbons and halohydrocarbons, such as tetrachloroethane, methylene chloride, chloroform, dichloroethane, chlorobenzene, 1,2- dichlorobenzene, benzene, toluene and xylene.

The activated carboxylic acid derivatives are usually isolated, for example by distilling the halogenating agent and, where present, the solvent and are then reacted with the amines.

In this case, the amidation is carried out at from −20 to 100° C., preferably from −10° to 20° C., in an inert aprotic polar organic solvent.

Halohydrocarbons, such as dichloromethane, and ethers, such as diethyl ether and tert-butyl methyl ether, are particularly suitable solvents for this reaction.

Since hydrogen halide is formed in the amidation of acyl halides, it is advisable to add the amine VIII in an excess of from 2 to 5, preferably from 2 to 3, mol equivalents. If the amine is used in a roughly equimolar amount (from 1 to 1.2 mol equivalents), a base, in particular a tertiary amine, such as triethylamine or pyridine, should be added to bind the hydrogen halide.

If a mixture of monesters IVa and IVb is used as the starting material, a mixture of the isomeric carboxamides is obtained in the reaction. This mixture can be separated into the individual components in a conventional manner, for example by fractional crystallization or chromatography.

The educts III required for this synthesis sequence are known (Bull Soc. Chim. Fr. 1974, 2079) or are obtainable by known methods (Bull Soc. Chim. Fr. 1969, 1762; J. Chem. Soc. 1953, 93).

b) Process for the preparation of thiazolecarboxamides IIe and IIf

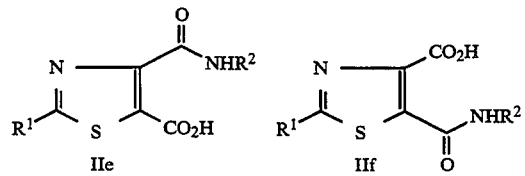

These thiazolecarboxamides IIe and IIf are obtained in a particularly advantageous manner by reacting the dicarboxylic anhydride of the formula V in a conventional manner with an amine of the formula VIII to give the isomers IIe and IIf and then separating the mixture into these isomers.

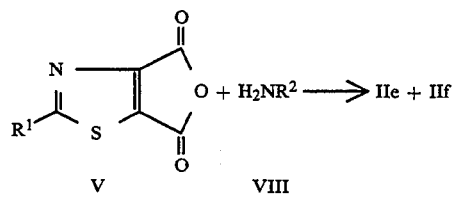

The reaction is usually carried out at from −10° to 150° C., preferably from 20° to 120° C., in an inert aprotic polar organic solvent.

Particularly suitable solvents are halohydrocarbons, e.g. tetrachloroethane, methylene chloride, chloroform, dichloroethane, chlorobenzene and 1,2-dichlorobenzene, ethers, e.g. diethyl ether, methyl tertbutyl ether, dimethoxyethane, diethylene glycol dimethyl ether, tetrahydrofuran and dioxane, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one, aromatics, e.g. benzene, toluene, xylene, pyridine and quinoline, ketones, e.g. acetone, methyl ethyl ketone, or corresponding mixtures.

The amine VIII is generally used in similar amounts or in excess, preferably in amounts of from 1.0 to 5.0 mol equivalents, based on V.

The dicarboxylic anhydrides required for this process are known or can be prepared by known methods (Bull. Soc. Chim. Fr. 1969, 1762; CS-A-195 369; CS-A-195 370).

c) Process for the preparation of the compounds IIe and IIf in which $R^1$ is not halogen or cyano:

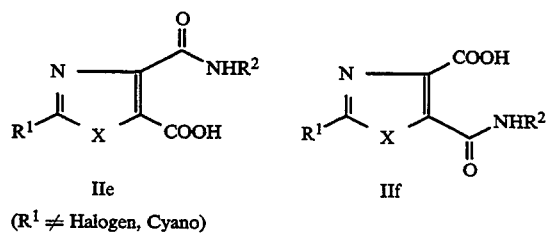

IIe   IIf ($R^1 \neq$ Halogen, Cyano)

These isomeric oxazole- or thiazolecarboxamides are obtained by activating and amidating a corresponding carboxylic acid under the conditions described for B and then reaction the resulting amides VIa and VIb in a conventional manner in the presence of a carboxylating reagent.

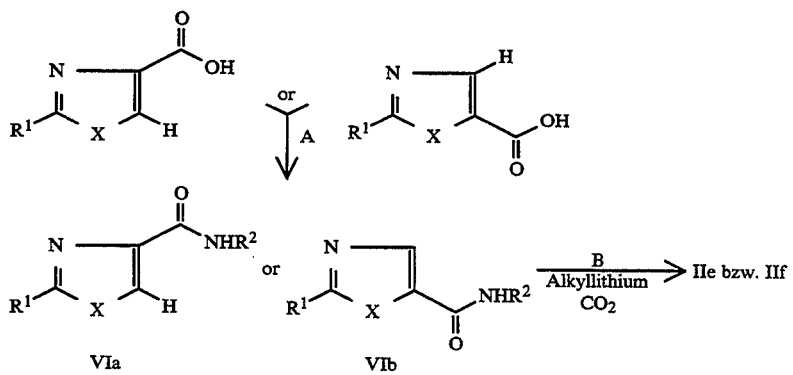

VIa   VIb

Reaction step A of the synthesis sequence is carried out in general and in particular under the conditions described in process a) under Section B.

Reaction step B:

The carboxylation of the oxazole- or thiazolecarboxamides VIa and VIb is carried out as a rule from 0° to −100° C., preferably from −50° to −80° C., in an aprotic polar inert organic solvent in the presence of a base in the absence of moisture.

A preferred carboxylating reagent is gaseous or solid carbon dioxide.

Particularly suitable solvents are ethers, e.g. diethyl ether, methyl tert-butyl ether, dimethoxyethane, diethylene glycol dimethyl ether, tetrahydrofuran and dioxane.

Preferably used based are organometallic compounds, such as methyllithium, n-butyllithium, sec-butyllithium, tert-butyllithium and phenyllithium.

The reaction is usually carried out by a procedure in which not more than 3 mol equivalents of the dissolved based are first added to a solution of the oxazole- or thiazolecarboxamide VIa or VIb, a derivative metallized at the heterocycle being formed, which derivative reacts to give the desired produce IIe or IIf when the electrophilic carboxylating reagent is subsequently added.

The carobyxlic acids required for the above process are known from the literature (Beilstein Volume 27, 1st–5th Supplements) or can be prepared by known methods, for example by oxidation of the corresponding alcohols or aldehydes or by hydrolysis of the corresponding nitriles (J. V. Metzger in The Chemistry of Heterocyclic Compounds, Vol. 34, Part 1, Thiazole and its Derivatives, Arnold Weissberger and E. D. Ward, C. Taylor (Editor), John Wiley & Sons, page 519 et seq., I. J. Turchi in The Chemistry of Heterocyclic Compounds, Vol. 45, Oxazoles, Arnold Weissberger and E. D. Ward, C. Taylor (Editor), John Wiley & Sons).

d) Compounds of the formula IIf can also be obtained by reacting corresponding dicarboxylates in a conventional manner with amines and hydrolyzing the resulting amides:

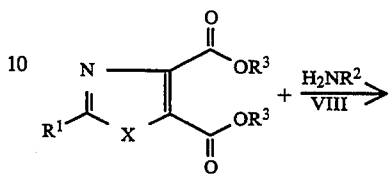

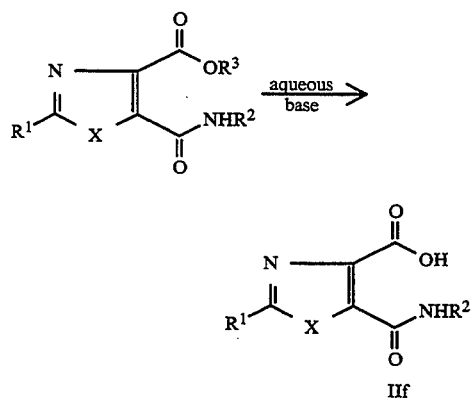

IIf ($R^3$ = $C_1$–$C_6$-alkyl)

Advantageously, the diester is dissolved in an inert organic solvent and reacted with an amine VIII.

Solvents used for these reactions are ethers, e.g. diethyl ether, methyl tert-butyl ether, dimethoxyethane, diethylene glycol dimethyl ether, tetrahydrofuran and dioxane; aromatics, e.g. benzene, toluene, xylene or mesitylene, alcohols, e.g. methanol, ethanol, isopropanol and tert-butanol, or corresponding mixtures.

The reaction can be carried out at from −100° C. up to the reflux temperature of the particular solvent or solvent mixture, preferably at from −60° to 150° C.

The molar ration in which the diester and the amine are used is in general from 1:1 to 1:2, preferably from 1:1 to 1:1.2.

The concentration of the educts in the solvent is in general from 0.1 to 5, preferably from 0.2 to 2.0, mol/l.

The reaction is particularly preferably carried out in an alcohol, such as ethanol, in the presence of one equivalent of an amine at from 50° to 100° C. The diesters required for the reaction are known from the literature or can be prepared similarly to methods described (Bull. Soc. Chim. Fr. 1969, 1762; J. Chem. Soc. 1953, 93).

In addition to the processes a–d described above for the preparation of the starting compounds IIe and IIf, there are further possible syntheses, which are described in the following publications:

Beilstein, main work and 1st–5th Supplements, Volume 27; R. W. Wiley, The Chemistry of Heterocyclic Compounds, Five- and Six-Membered Compounds with Nitrogen and Oxygen, Interscience Publishers, New York, London (1962); Heterocyclic Chemistry, Vol. 6, Five-membered Rings with Two or More Oxygen, Sulfur or Nitrogen Atoms, Pergamon Press, 1984; J. March, Advanced Organic Chemistry, Third edition, John Wiley & Sons, 1985; Houben-Weyl, Methoden der organischen Chemie, 4th edition, Thieme Verlag, Volumes IV, VI, VII, VIII and X; DE-A-39 32 052.

Route B

A further process for the synthesis of compounds of the formula Ia comprises reacting hydroxamyl chlorides X with halomaleimides XI. In an advantageous procedure, the halomaleimide XI in an inert organic solvent is initially taken, roughly molar amounts of the hydroxamyl chloride X are added and about twice the molar amount of a base is then added dropwise. The mixture can be worked up in a conventional manner, for example by hydrolyzing with water and filtering off the produce under suction or extracting it with an organic solvent and evaporating the organic solvent.

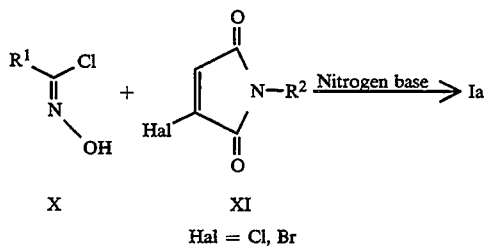

Hal = Cl, Br

Advantageously used solvents for these reactions are halohydrocarbons, such as dichloroethane, chlorobenzene, 1,2-dichlorobenzene, tetrachloroethane, dichloromethane and chloroform, ethers, such as diethyl ether, methyl tert-butyl ether, dimethoxyethane, diethylene glycol dimethyl ether, tetrahydrofuran and dioxane, or aromatics, such as benzene, toluene and xylene, or mixtures of these solvents.

The reactions can be carried out at from −10° C. to 50° C., preferably from 0° to 30° C.

Preferred bases are nitrogen bases, such as 2-, 3- and 4-picoline, N,N-dimethylaniline, N,N-dimethylcyclohexylamine, triethylamine (TEA), pyridine and 1,8-diazabicyclo[5.4.0]undec-7-ene (DBU).

The reactants are used in particular in a molar ratio of 1:1, and the nitrogen base is added in from two to three times the molar amount.

The concentration of the educts in the solvent mixture is in general from 0.1 to 5, preferably from 0.2 to 2, mol/l.

Route C

A further process for the synthesis of the compounds Ia comprises oxidizing isoxazolinedicarboximides XII, which are prepared, for example, by reacting hydroxamyl chlorides X with maleimides XIII. In an advantageous procedure, the maleimide XIII in an inert organic solvent is initially taken, roughly molar amounts of the hydroxamyl chlorides X are added and about a molar amount of a base is then added dropwise. The mixture can be worked up in a conventional manner, for example by hydrolyzing with water and filtering off the product under suction or extracting it with an organic solvent.

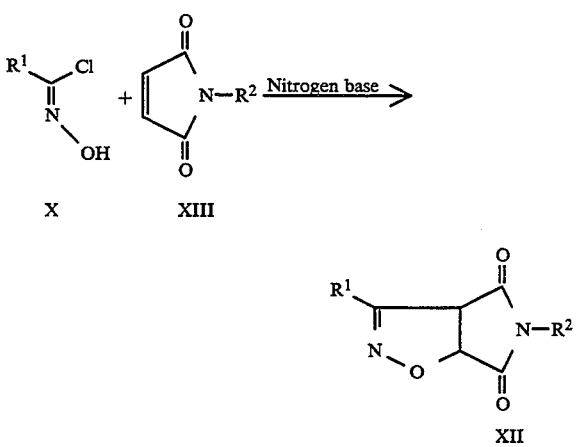

Advantageously used solvents for these reactions are halohydrocarbons such as tetrachloroethane, dichloromethane, dichloroethane, chlorobenzene, 1,2-dichlorobenzene and chloroform, or aromatics, such as benzene, toluene and xylene, or mixtures of these solvents.

The reactions can be carried out at from −10° to 50° C., preferably from 0° C. to 30° C.

Suitable bases are nitrogen bases such as 2-, 3- and 4-picoline, N,N-dimethylaniline, N,N-dimethylcyclohexylamine, triethylamine (TEA), pyridine and 1,8-diazabicyclo[5.4.0]undec-7-ene (DBU).

The reactants are used in particular in molar ratios of from 1:1 to 1.1:1 (maleimide:hydroxamyl chloride), and the nitrogen base is added in the molar amount to twice the molar amount.

The concentration of the educts in the solvent mixture is in general from 0.1 to 5, preferably from 0.2 to 2, mol/l.

The isoxazoledicarboximides Ia are obtainable by dehydrogenating the isoxazolinimides XII. In an advantageous procedure, the isoxazolinimide XII in an inert organic solvent is initially taken and about a molar amount of an oxidizing agent is added.

Suitable solvents for the dehydrogenation are in particular aromatic hydrocarbons, such as benzene, toluene or xylene.

Preferably used oxidizing agents are sodium hypochlorite, nitrobenzene or quinones, such as 2,3,5,6-tetrachloro-p-benzoquinone or 5,6-dichloro-2,3-dicyano-p-benzoquinone (DDQ).

The reactions can be carried out at from 50° C. to the boiling point of the solvent used.

The reactants can be used in a molar ratio of from 1:1 to 1:10 (isoxazolinimide:oxidizing agent).

In view of the intended use of the compounds I, the following radicals are preferred substituents:

X is oxygen or sulfur, $R^1$ is halogen, such as fluorine, chlorine, bromine or iodine, in particular fluorine or chlorine, cyano, $C_1$–$C_6$-alkyl, such as methyl, ethyl, n-propyl, isopropyl, n-butyl, sec-butyl, isobutyl or tert-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl, propyl or isopropyl, which may carry from one to five halogen atoms, in particular fluorine and/or chlorine atoms or one or two of the following radicals:

$C_3$–$C_8$-cycloalkyl, such as cyclopropyl, cyclobutyl, cyclopentyl or cyclohexyl, in particular cyclopropyl, $C_1$–$C_4$-alkoxy, such as methoxy, ethoxy, n-propoxy, 2-methylethoxy, n-butoxy, 1-methylpropoxy, 2-methylpropoxy or 1,1-dimethylethoxy, in particular methoxy, ethoxy, 1-methylethoxy or 1,1-dimethylethoxy, $C_1$–$C_4$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or pentafluoroethoxy, $C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio or ethylthio, $C_1$–$C_4$-haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio or pentafluoroethylthio, in particular trifluoromethylthio or pentafluoroethylthio, $C_1$–$C_4$-alkylsulfonyl, such as methylsulfonyl or ethylsulfonyl, in particular methylsulfonyl, $C_1$–$C_4$-haloalkylsulfonyl, such as trifluoromethylsulfonyl or pentafluoroethylsulfonyl, in particular trifluoromethylsulfonyl, or cyano, $C_3$–$C_6$-cycloalkyl, such as cyclopropyl, cyclobutyl, cyclopentyl, cyclohexyl, cycloheptyl or cyclooctyl, in particular cyclopropyl, cyclopentyl or cyclohexyl, which may carry from one to three of the following radicals:

alkyl as stated above, in particular methyl, or halogen as stated above, in particular chlorine or fluorine, $C_3$–$C_8$-alkenyl, such ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-2-butenyl, 1-methyl-2-butenyl, 2-methyl-2-butenyl, 1-methyl-3-butenyl, 2-methyl-3-butenyl, 3-methyl-3-butenyl, 1,1-dimethyl-2-propenyl, 1,1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 1,3-dimethyl-1-butenyl, 2,3-dimethyl-1-butenyl, 2,3-dimethyl-2-butenyl, 2,3-dimethyl-3-butenyl. 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2,2-propenyl, 1-ethyl-1-methyl-2-propenyl, 1-ethyl-2-methyl-1-propenyl or 1-ethyl-2-methyl-2-propenyl, in particular 2-propenyl, which may carry from one to three of the following radicals: halogen as stated above, in particular fluorine or chlorine, alkoxy as stated above, in particular methoxy or ethoxy, and/or phenyl which in turn may carry from one to three of the following groups: alkyl as stated above, in particular methyl, ethyl or isopropyl, haloalkyl as stated above, in particular trifluoromethyl or chlorodifluoromethyl, alkoxy as stated above, in particular methoxy or ethoxy, haloalkoxy as stated above, in particular trifluoromethoxy, pentafluoroethoxy or trichloromethoxy, alkylthio as stated above, in particular methylthio or ethylthio, haloalkylthio as stated above, in particular difluoromethylthio, pentafluoroethylthio or trifluoromethylthio, halogen as stated above, in particular fluorine or chlorine, cyano or nitro, $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-alkynyl, 4-hexynyl, 1-methyl-2-pentynyl, 1-methyl-3-pentynyl, 1-methyl-4-pentynyl, 2-methyl-3-pentynyl, 2-methyl-4-pentynyl, 3-methylpentynyl, 3-methyl-4-pentynyl, 4-methyl-1-pentynyl, 4-methyl-2-methyl-2-pentynyl, 1,1-dimethyl-2-butynyl, 1,1-dimethyl-3-butynyl, 1,2-dimethyl-3-butynyl, 2,2-dimethyl-4-butynyl, 3,3-dimethyl-1-butynyl, 1-ethyl-2-butynyl, 1-ethyl-3-butynyl, 2-ethyl-3-butynyl or 1-ethyl-1-ethyl-1-methyl-2-propynyl, in particular 2-propynyl, which may carry from one to three of the following radicals: halogen as stated above, in particular iodine, alkoxy as stated above, in particular methoxy or ethoxy, and/or phenyl which in turn may carry from one to three of the following groups: alkyl as stated above, in particular methyl, ethyl or isopropyl, haloalkyl as stated above, in particular trifluoromethyl or chlorodifluoromethyl, alkoxy as stated above, in particular methoxy or ethoxy, haloalkoxy as stated above, in particular trifluoromethoxy, pentafluoroethoxy or trichloromethoxy, alkylthio as stated above, in particular methylthio or ethylthio, haloalkylthio as stated above, in particular difluoromethylthio, pentafluoroethylthio or trifluoromethylthio, halogen as stated above, in particular fluorine or chlorine, cyano or nitro, $C_2$–$C_6$-alkenyloxy, such as vinyloxy, 2-propenyloxy, 2-methyl-2-propenyloxy, (E)-2-butenyloxy, (Z)-2-butenyloxy, 1,3-dimethyl-2-butenyloxy, 2-pentenyloxy or 2-hexenyloxy, in particular 2-propenyloxy and (E)-2-butenyloxy, $C_3$–$C_6$-alkynyloxy, such as 2-propynyloxy, 2-butynyloxy, 1-ethyl-2-butynyloxy, 1-methyl-2-propynyloxy, 2-pentynyloxy or 2-hexynyloxy, in particular 2-propynyloxy, $C_1$–$C_4$-alkylthio as stated above, in particular methylthio or ethylthio $C_1$–$C_4$-haloalkylthio as stated above, in particular difluoromethylthio, pentafluoroethylthio or trifluoromethylthio, $C_1$–$C_4$-alkylsulfonyl as stated above, in particular methylsulfonyl, $C_1$–$C_4$-haloalkylsulfonyl as stated above, in particular trifluoromethylsulfonyl, phenoxy or phenylthio, where these radicals may carry from one to three of the following groups: $C_1$–$C_4$-alkyl as stated above, in particular methyl, ethyl or isopropyl, $C_1$–$C_4$-haloalkyl as stated above, in particular trifluoromethyl or chlorodifluoromethyl, $C_1$–$C_4$-alkoxy as stated above, in particular methoxy or ethoxy, $C_1$–$C_4$-haloalkoxy as stated above, in particular trifluoromethoxy, pentafluoroethoxy or trichloromethoxy, $C_1$–$C_4$-alkylthio as stated above, in particular methylthio or ethylthio, $C_1$–$C_4$-haloalkylthio as stated above, in particular difluoromethylthio, pentafluoroethylthio or trifluoromethylthio, halogen as stated above, in particular fluorine or chlorine, cyano or nitro, a 5-membered or 6-membered heterocyclic radical which contains one or two hetero atoms selected from the group consisting of oxygen, sulfur and nitrogen, such as 2-tetrahydrofuranyl, 3-tetrahydrofuranyl, 4-tetrahydropyranyl, 2-tetrahydropyranyl, 3-tetrahydropyranyl, 3-furanyl, 2-thienyl, 3-thienyl, 2-furanyl, 3-tetrahydrothienyl, 3-sulfolanyl, 2-tetrahydropyranyl, 5-isoxazolyl, 3-isoxazolyl, 4-isoxazolyl, 5-isothiazolyl, 4-isothiazolyl, 3-isothiazolyl, 2-oxazolyl, 4-thiazolyl, 4-oxazolyl, 2-thiazolyl, 5-oxazolyl, 5-thiazolyl, 2-imidazolyl, 4-imidazolyl, 5-imidazolyl, 3-pyrrolyl, 2-pyrrolyl, 3-pyrazolyl, 4-pyrazolyl, 5-pyrozolyl, 4-pyridyl, 3-pyridyl or 2-pyridyl, where these rings may carry one or two of the following radicals: alkyl as stated above, in particular methyl, halogen as stated above, in particular fluorine or chlorine, alkoxy as stated above, in particular methoxy or ethoxy, or alkoxycarbonyl, such as methoxycarbonyl, or ethoxycarbonyl, in particular methoxycarbonyl, a fused aromatic radical selected from the group consisting of benzofuran-2-yl, benzofuran-3-yl, isobenzofuran-2-yl, benzothiophen-2yl, benzothiophen-3-yl, isobenzothiophen-2-yl, indol-2-yl, indol-3-yl, 1,2-benzoisoxal-3-yl, benzoxazol-2-yl, 1,2-benzoisothiazol-3-yl, benzothiazol-2-yl, indazol-3yl, (1H)-benzimidazol-2yl, quinol-3-yl, quinol-5-yl, quinol-6-yl, quinol-8-yl, isoquinol-1-yl and isoquinol-5-yl, where this radical may carry one or two of the following radicals: alkyl as stated above, in particular methyl, halogen as stated above, in particular fluorine or chlorine, alkoxy as stated above, in particular methoxy or ethoxy, or alkoxycarbonyl, such as methoxycarbonyl or ethoxycarbonyl, in particular methoxycarbonyl, phenyl or phenyl-$C_1$–$C_4$-alkyl, e.g. benzyl or phenylethyl, where the phenyl radical in each case may carry from one to three of the following groups: alkyl as stated above, in particular methyl, ethyl or isopropyl, haloalkyl as stated above, in particular trifluoromethyl or chlorodifluoromethyl, alkoxy as stated above, in particular methoxy or ethoxy, haloalkoxy as stated above, in particular trifluoromethoxy, pentafluoroethoxy or trichloromethoxy, alkylthio as stated above, in particular methylthio or ethylthio, haloalkylthio as stated above, in particular difluoromethylthio, pentafluoroethylthio or trifluoromethylthio, halogen as stated above, in particular fluorine or chlorine, cyano or nitro, $R^2$ is hydrogen, hydroxyl, $C_1$–$C_4$-alkoxy as stated under $R^1$, in particular methoxy or ethoxy, $C_1$–$C_6$-alkyl as stated under $R^1$, in particular methyl, ethyl, propyl, 1-methylethyl, butyl, 1-methylpropyl, 2-methylpropyl or 1,1-dimethylethyl, 1,1-dimethylpropyl, 1,1-dimethylbutyl, 1,2-dimethylopropyl, which may carry from one to three of the following groups: cyano, alkoxyalkoxy, such as methoxymethoxy or ethoxyethoxy, in particular methoxymethoxy, alkoxy as stated under $R^1$, in particular methoxy or ethoxy, haloalkoxy as stated under $R^1$, in particular trifluoromethoxy, alkylthio as stated under $R^1$, in particular methylthio or ethylthio, haloalkylthio as stated under $R^1$, in particular trifluoromethylthio, dialkylamino, in particular dimethylamino or diethylamino, halogen as stated under $R^1$, in particular fluorine or chlorine, cycloalkyl as stated for $R^1$, in particular cyclopropyl, cyclopentyl or cyclohexyl, or phenyl which in turn may carry from one to three of the following groups: halogen, cyano, nitro, alkyl as stated under $R^1$, in particular methyl or ethyl, haloalkyl as stated under $R^1$, in particular trifluoromethyl, alkoxy as stated under $R^1$, in particular methoxy or ethoxy, haloalkoxy as stated under $R^1$, in particular trifluoromethoxy, alkylthio as stated under $R^1$, in particular methylthio or ethylthio, or haloalkylthio as stated under $R^1$, in particular trifluoromethylthio, $C_3$–$C_8$-cycloalkyl as stated under $R^1$, in particular cyclopropyl, cyclobutyl, cyclopentyl or cyclohexyl, which may carry from one to three of the following groups:

alkyl as stated under $R^1$, in particular methyl, ethyl or 1-methylethyl, haloalkyl as stated under $R^1$, in particular trifluoromethyl, alkoxy as stated under $R^1$, in particular methoxy or ethoxy, haloalkoxy as stated under $R^1$, in particular trifluoromethoxy, halogen as stated under $R^1$, in particular fluorine or chlorine, nitro or cyano, $C_3$–$C_6$-alkenyl as stated under $R^1$, in particular 2-propenyl, 1-methyl-2-propenyl, 1,1-dimethyl-2-propenyl or 2-butenyl, which may be monosubstituted to trisubstituted by halogen as stated under $R^1$, in particular fluorine or chlorine, and/or monosubstituted by phenyl, where the phenyl radical in turn may carry from one to three of the following groups: alkyl as stated under $R^1$, in particular methyl or ethyl, haloalkyl as stated under $R^1$, in particular trifluoromethyl, alkoxy as stated under $R^1$, in particular methoxy or ethoxy, haloalkoxy as stated under $R^1$, in particular trifluoromethoxy, alkylthio as stated under $R^1$, in particular methylthio or ethylthio, haloalkylthio as stated under $R^1$, in particular trifluoromethylthio, halogen as stated under $R^1$, in particular fluorine or chlorine, cyano or nitro, $C_3$–$C_6$-alkynyl as stated under $R^1$, in particular 2-propynyl, 1-methyl-2-propynyl or 1,1-dimethyl-2-propynyl, which may be monosubstituted to trisubstituted by halogen as stated under $R^1$, in particular fluorine or chlorine, and/or monosubstituted by phenyl, where the phenyl radical in turn may carry from one to three of the following groups: alkyl as stated under $R^1$, in particular methyl or ethyl, haloalkyl as stated under R¹, in particular trifluoromethyl, alkoxy as stated under R¹, in particular methyl or ethyl, haloalkyl as stated under R¹, in particular trifluoromethyl, alkoxy as stated under R¹, in particular methoxy or ethoxy, haloalkoxy as stated under R¹, in particular methylthio or ethylthio, haloalkylthio as stated under R¹, in particular trifluoromethylthio, halogen as stated under R¹, in particular fluorine or chlorine, cyano or nitro, $C_1-C_4$-dialkylamino, in particular dimethylamino or diethylamino, a 5-membered or 6-membered heterocyclic radical having one or two hetero atoms selected from the group consisting of oxygen, sulfur and nitrogen, as stated under R¹, which may be monosubstituted to trisubstituted by alkyl as stated under R¹, in particular methyl, ethyl or 1-methylethyl, or halogen as stated under R¹, in particular fluorine or chlorine, a fused aromatic radical selected from the group consisting of benzofuran-2-yl, benzofuran-3-yl, isobenzofuran-2-yl, benzothiophen-2-yl, benzothiophen-3-yl, isobenzothiophen-2-yl, indol-2-yl, indol-3-yl, 1,2-benzoisoxal-3-yl, benzoxazol-2-yl, 1,2-benzoisothiazol-3-yl, benzothiazol-2-yl, indazol-3-yl, (1H)-benzimidazol-2-yl, quinol-3-yl, quinol-5-yl, quinol-6-yl, quinol-8-yl, isoquinol-1-yl and isoquinol-5-yl, where this radical may be monosubstituted to trisubstituted by $C_1-C_4$-alkyl or halogen, phenyl which may carry from one to four of the following groups: alkyl as stated under R¹, in particular methyl, ethyl or 1-methylethyl, haloalkyl as stated under R¹, in particular trifluoromethyl, alkoxy as stated under R¹, in particular methoxy or ethoxy, haloalkoxy as stated under R¹, in particular trifluoromethoxy, alkylthio as stated under R¹, in particular methylthio or ethylthio, haloalkylthio as stated under R¹, in particular trifluoromethylthio, halogen as stated under R¹, in particular fluorine or chlorine, nitro, cyano, formyl, $C_1-C_4$- alkanoyl, such as acetyl, propionyl or butyryl, in particular acetyl, haloalkanoyl, such as trifluoroacetyl, trichloroacetyl or pentafluoropropionyl, in particular trifluoroacetyl, or alkoxycarbonyl as stated under R¹, in particular methoxycarbonyl, or naphthyl which may be monosubstituted to trisubstituted by alkyl as stated under R¹, in particular methyl or ethyl, or halogen as stated under R¹, in particular fluorine or chlorine.

Examples of herbicidal compounds of the formulae Ia and Ib are stated below specifically:

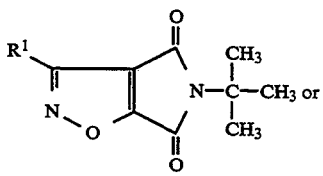

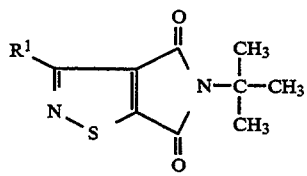

where R¹ in each case is hydrogen, fluorine, chlorine, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cylcopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-metylopropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

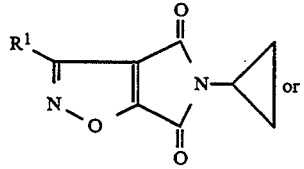

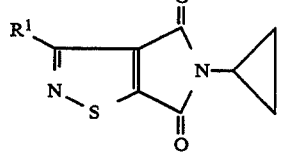

where R¹ in each case is hydrogen, fluorine, chlorine methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methoxyethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2- fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

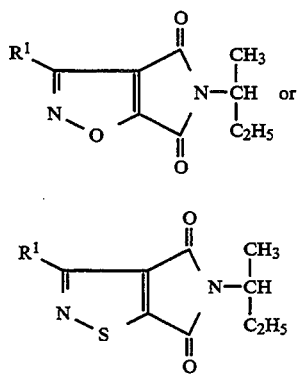

where R¹ in each case is hydrogen, fluorine, chlorine, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-metylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

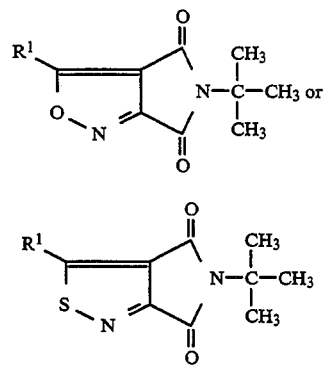

where R¹ in each case is hydrogen, fluorine, chlorine, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

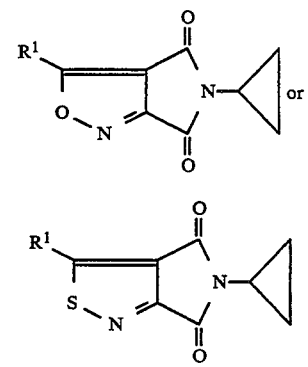

where R¹ in each case is hydrogen, fluorine, chlorine, methyl, ethyl, propyl, 1-methylethyl, butyl, 1-methylpropyl, 2-methylpropyl, 1,1-dimethylethyl, pentyl, 1- methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-diochlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

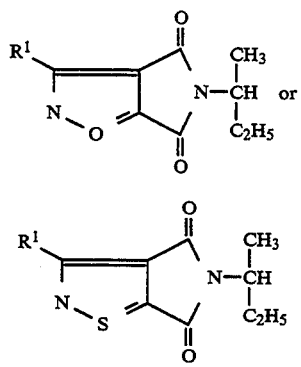

where $R^1$ in each case is hydrogen, fluorine, chlorine, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

Examples of herbicidal compounds of the formula Ic are specific e:

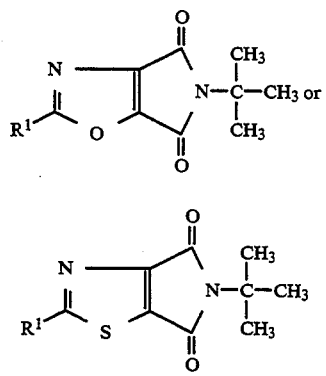

where $R^1$ in each case is hydrogen, fluorine, chlorine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,1-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

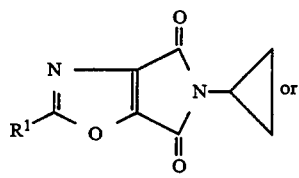

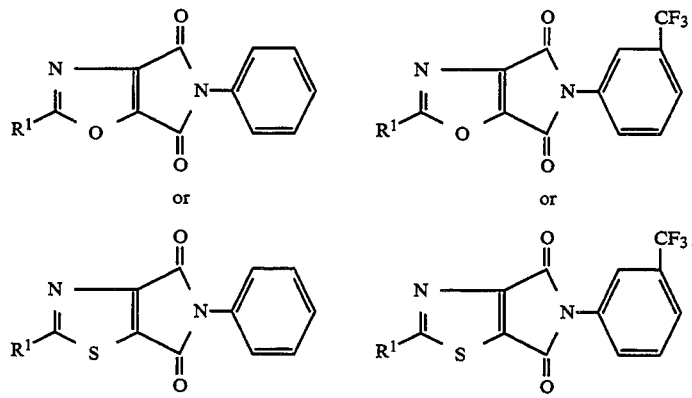

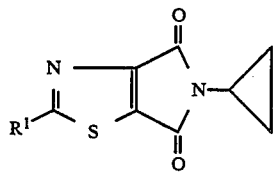

where R¹ in each case is hydrogen, fluorine, chlorine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

where R¹ in each case is hydrogen, fluorine, chlorine, cyano, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)ethyl, chloromethyl, dichloromethyl, trichloromethyl, chlorodifluoromethyl, trifluoromethyl, pentafluoroethyl, difluoromethyl, 1-chloroethyl, 2-chloroethyl, 1-methyl-1-chloroethyl, 1-methyl-2-chloroethyl, methoxymethyl, 1-methylmethoxymethyl, 1-methyl-2-methoxyethyl, 1-methylethoxymethyl, ethoxymethyl, ethenyl, 1-propenyl, 2-propenyl, 1-methylethenyl, 1-ethylethenyl, 2-phenylethenyl, 1-butenyl, 2-butenyl, 3-butenyl, 1-methyl-1-propenyl, 1-methyl-2-propenyl, 2-methyl-2-propenyl, 2-propynyl, methoxy, ethoxy, propoxy, 1-methylethoxy, butoxy, 1-methylpropoxy, 1,1-dimethylethoxy, methylthio, ethylthio, chlorodifluoromethoxy, trifluoromethoxy, trichloromethylthio, phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-trifluoromethylphenyl, 3-trifluoromethylphenyl, 4-trifluoromethylphenyl, 2-methoxyphenyl, 3-methoxyphenyl, 4-methoxyphenyl, 2,4-dichlorophenyl, 2,4,6-trimethylphenyl, phenoxy, phenylthio, 2-chlorophenoxy, 3-chlorophenoxy, 4-chlorophenoxy, 2,4-dichlorophenoxy, benzyl, 2-chlorobenzyl, 3-chlorobenzyl, 4-chlorobenzyl, 2-fluorobenzyl, 3-fluorobenzyl, 4-fluorobenzyl, 2-thienyl, 3-thienyl, 2-pyridyl, 3-pyridyl or 4-pyridyl;

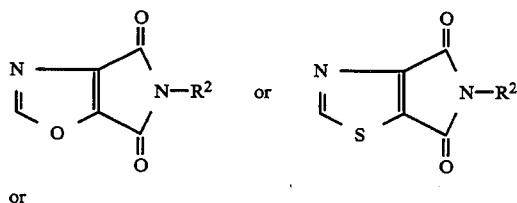

or

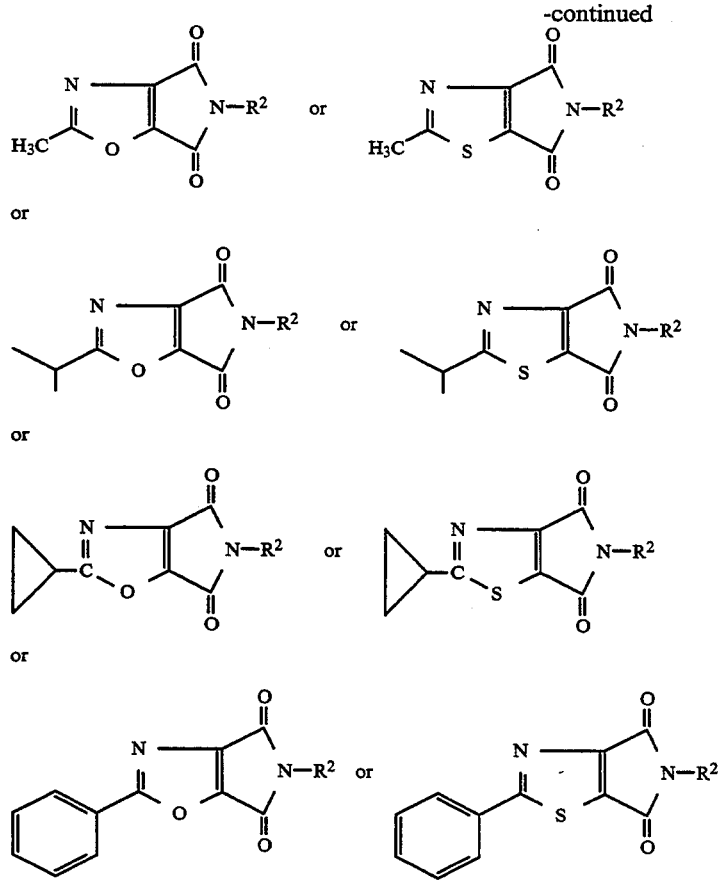

where R² in each case is methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cycloheptyl, cyclooctyl, 1-methylcyclopropyl, cyclopropylmethyl, 1-(cyclopropyl)-ethyl, 1-methylcyclohexyl, 1-ethylcyclohexyl, cyclohexylmethyl, 2-propenyl, 1-methyl-2-propenyl, 1,1-dimethyl-2-propenyl, 2-propynyl, 1-methyl-2-propynyl, 1,1-dimethylpropynyl, phenylmethyl, 1-methylphenylmethyl, 1,1-dimethylphenylmethyl, 2-phenylethyl, 2-methylthioethyl, 1-methyl-2-methylthioethyl, 1,1-dimethyl-2-methylthioethyl, 3-methylthiopropyl, 2-fluoroethyl, 2-fluoro-1-methylethyl, 1,1-dimethyl-2-fluoroethyl, 2-chloroethyl, 2-chloro-1-methylethyl, 2-chloro-1,1-dimethylethyl, 2-methoxyethyl, 2-methoxy-1-methylethyl, 1,1-dimethyl-2-methoxyethyl, 3-methoxypropyl, 2-cyanoethyl, 2-cyano-1-methylethyl, 2-cyano-1,1-dimethylethyl, dimethylamino, diethylamino, morpholino, piperidino, phenyl, 2-methylphenyl, 3-methylphenyl, 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,4,5-trimethylphenyl, 2,4,6-trimethylphenyl, 3,4,5-trimethylphenyl, 2-trifluoromethylphenyl, 3-trifluoromethylphenyl, 4-trifluoromethylphenyl, 2-fluorophenyl, 3-fluorophenyl, 4-fluorophenyl, 2-chlorophenyl, 3-chlorophenyl, 4-chlorophenyl, 2,3-difluorophenyl, 2,4-difluorophenyl, 2,5-difluorophenyl, 2,6-difluorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,4,6-trichlorophenyl, 3,4,5-trichlorophenyl, 2-cyanophenyl, 3-cyanophenyl, 4-cyanophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4,5-dimethoxyphenyl, 2-trifluoromethoxyphenyl, 3-trifluoromethoxyphenyl, 4-trifluoromethoxyphenyl, 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 3,5-dinitrophenyl, 1-naphthyl, 2-naphthyl, 3-tetrahydrofuryl, 4-tetrahydropyranyl or 2-thiazolyl.

The abovementioned definitions of the radicals R¹ and R² may furthermore be combined with one another in the oxazole- or thiazole-4,5-dicarboximides to give combinations other than those listed.

Suitable salts of the compounds of the formulae Ia, Ib and Ic are agriculturally useful salts, for example alkali metal salts, such as the potassium or sodium salt, alkaline earth metal salts, such as the calcium, magnesium or barium salt, manganese salts, copper salts, zinc salts or iron salts and ammonium, phosphonium sulfonium and sulfoxonium salts, for example ammonium salts tetraalkylammonium salts, benzyltrialkylammonium salts, trialkylsulfonium salts or trialkylsulfoxonium salts.

The novel herbicidal compounds or the agents containing them can be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds are suitable in general for the preparation of directly sprayable solutions, emulsions, pastes or oily dispersions. Suitable inert additives are mineral oil fractions having a medium to high boiling point, such as kerosene or diesel oil, as well as coal tar oils and oils of vegetable or animal origin, aliphatic, cycloaliphatic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene or isophorone, or strongly polar solvents, such as N,N-dimethylformamide, dimethyl sulfoxide, N-methylpyrrolidone or water.

Aqueous application forms can be prepared from emulsion concentrates, dispersion, pastes, wettable powders or water-dispersable granules by the addition of water. For the preparation of emulsions, pastes or oil dispersions, the substrates, as such or in solution in an oil or solvent, can be homogenized in water by means of wetting agents, adhesives, dispersants or emulsifiers. However, it is also possible to prepare concentrates which consist of active substance, wetting agents, adhesives, dispersants or emulsifiers and possibly a solvent or oil and which are suitable for dilution with water.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, laurylethersulfates and fatty alcohol sulfates, and salts of sulfates hexa-, hepta- and octadecanols, and of fatty alcohol glycol ethers, condensates of sulfonated naphthalene and of its derivatives with formaldehyde, condensates of naphthalene or of naphthalensulfonic acids with phenol and formaldehyde, polyoxyethylene octylphenol ethers, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as cereal meal, ground bark, woodmeal, nutshell meal and cellulose powder, or other solid carriers.

The formulations contain from 0.1 to 95, preferably from 0.5 to 90, % by weight of active ingredient. The active ingredients are used in a purity of from 90 to 100%, preferably from 95 to 100% (according to NMR spectrum).

The novel compounds I can be formulated, for example as follows:

I. 90 parts by weight of compound No. 1.001 are mixed with 10 parts by weight of N-methyl-α-pyrrolidone, and a solution which is suitable for use in the form of very small drops is obtained.

II. 20 parts by weight of compound No. 4.003 are dissolved in a mixture which consists of 80 parts by weight of xylene, 10 parts by weight of an adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 1.001 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 4.003 are dissolved in a mixture which consists of 25 parts by weight of cyclohexanone, 65 parts by weight of a mineral oil fraction boiling within a range from 210° to 280° C., and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 1.001 are thoroughly mixed with 3 parts by weight of the sodium salts of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.001 are mixed with 97 parts by weight of finely divided kaolin. A dusting agent which contains 3% by weight of the active ingredient is obtained in this manner.

VII. 30 parts by weight of active ingredient No. 4.003 are thoroughly mixed with a mixture of 92 parts by weight of silica gel powder and 8 parts by weight of liquid paraffin which has been sprayed onto the surface of the silica gel. A formulation of the active ingredient having good adhesion is obtained in this manner.

VIII. 20 parts by weight of active ingredient No. 4.003 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicidal and growth-regulating agents or the active ingredients can be applied by the preemergence of postemergence method. If the active ingredients are less well tolerated by certain crops, it is possible to use application methods in which the herbicides are sprayed with the aid of sprayers in such a way that the leaves of the sensitive crops are as far as possible not affected while the active ingredients reach the leaves of undesirable plants growing underneath or the uncovered soil surface (post-directed, lay-by).

The application rates of active ingredient when used as herbicides are from 0.001 to 3, preferably from 0.1 to 2, kg/ha of active substance (a.s.), depending on the aim of control, the season, the target plants and the stage of growth.

In view of the available action spectrum for weed control, the toleration by crops or the desired effect on the growth of the crops and because of the variety of application methods, the novel compounds can be used in a large number of crops. For example, the following crops are suitable:

| Botanical name | Common name |
| --- | --- |
| Allium cepa | onions |
| Ananas comosus | pineapples |
| Arachis hypogaea | peanuts (groundnuts) |
| Asparagus-officinalis | asparagus |
| Beta vulgaris spp. altissima | sugar beet |
| Beta vulgaris spp. rapa | fodder beet |
| Brassica napus var. napus | rapeseed |
| Brassica napus var. napobrassica | swedes |
| Brassica rapa var. silvestris | turnip rape |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermuda grass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regla | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustics) | tobacco |
| Olea europaea | olive trees |
| Oryza sativa | rice |
| Phaseolus lunatus | Sievabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus dulcis | almond trees |
| Prunus persica | peach trees |
| Pyrus communis | pear trees |
| Ribes sylvestre | redcurrants |

-continued

| Botanical name | Common name |
| --- | --- |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To extend the action spectrum and to achieve synergistic effects, the compounds of the formula I can be mixed both with one another and with members of other groups of herbicidal or growth-regulating active ingredients and applied together with these. Examples of suitable components for the mixture are diazine, 4H-3, 1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, sulfonylurea derivatives, (hetero)aryloxyphenoxypropionic acids and salts, esters and amides thereof and others.

It may also be useful to apply the compounds I, alone or in combination with other herbicides, also as a mixture with other crop protection agents, for example with pesticides or agents for controlling phytopathogenic fungi or bacteria. The miscibility with mineral salt solutions which are used for eliminating nutrient and trace element deficiencies is also of interest. Non-phytotoxic oils and oil concentrates may also be added.

The Examples which follow illustrate the preparation of the compounds I.

1. Preparation of the compounds Ia and Ib

N-tert-Butyl-3-isopropylisoxazole-4,5-dicarboximide 7.5 g (74.1 mmol) of methylmorpholine, 2.4 g (20 mmol) of dimethylaminopyridine and 17.4 g of a 50% strength solution of propanephosphonic anhydride (27.3 mmol) in dichloromethane were add dropwise in succession to 5.1 g (20 mmol) of 5-tert-butylaminocarbonyl-3-isopropylisoxazole-4-carboxylic acid in 200 ml of dichloromethane at $-5°$ C., and the mixture was then refluxed for 6 hours. The solvent was stripped off under reduced pressure, the residue was taken up in 300 ml of ethyl acetate and the solution was extracted twice with saturated sodium bicarbonate solution and once each with 5% strength citric acid solution, saturated sodium carbonate solution and saturated sodium chloride solution. The organic phase was dried and the solvent was stripped off under reduced pressure. 4.1 g (87%) of N-tert-butyl-3-isopropylisoxazole-4,5-dicarboximide were obtained as a solid of melting point 60°–62° C. (Example No. 1.003).

5.5 g (45.3 mmol) of 2-methylpropylhydroxamyl chloride in 100 ml of toluene were added to 8.5 g (45.3 mmol) of N-tert-butylchloromaleimide in 100 ml of dry toluene at 0° C. Thereafter, 9.6 g (94.9 mmol) of triethylamine were added dropwise at 0° C. and the mixture was stirred for 12 hours at room temperature. It was filtered, the filtrate was extracted with 10% HCl, the organic phase was dried over magnesium sulfate and the solvent was stripped off under reduced pressure. 7.9 g (74%) of N-tert-butyl-3-isopropylisoxazole-4,5-dicarboximide (physical data, see above) were obtained.

N-tert-Butyl-3-isopropylisothiazole-4,5-dicarboximide 7.5 g (74.1 mmol) of methylmorpholine, 2.4 g (20 mmol) of dimethylaminopyridine and 17.4 g of a 50% strength solution of propanephosphonic anhydride (27.3 mmol) in dichloromethane were added dropwise in succession to 5.4 g (20 mmol) of 5-tert-butylaminocarbonyl-3-isopropylisothiazole-4-carboxylic acid in 200 ml of dichloromethane at −5° C. and the mixture was then refluxed for 6 hours. Working up was carried out as described above for Example No. 1.003. 4.8 g (95%) of N-tert-butyl-3-isopropylisothiazole-4,5-dicarboximide were obtained as a solid of melting point 52°–53° C. (Example No. 3.001).

N-tert-Butyl-5-methylisoxazole-3,4-dicarboximide 6.3 g )62.2 mmol) of methylmorpholine, 2.4 g (20 mmol) of dimethylaminopyridine and 14.6 g of a 50% strength solution of propanephosphonic anhydride (23 mmol) in dichloromethane were added dropwise in succession to 3.8 g (16.8 mmol) of 3-tert-butylaminocarbonyl-5-methylisoxazole-4-carboxylic acid in 150 ml of dichloromethane at −5° C. and the mixture was then refluxed for 6 hours. Working up was carried out as described above. 3.2 g (91%) of N-tert-butyl-5-methylisoxazole-3,4-dicarboximide were obtained as a solid of melting point 48°–50° C. (Example No. 2.001).

It is also possible to prepare in a similar manner, for example, further compounds having the general structures

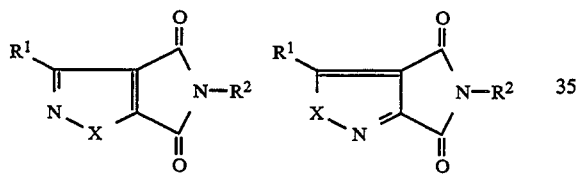

where X is oxygen or sulfur and, for example, $R^1$ is a radical of one of the groups $Q_1$ to $Q_{104}$, $R^2$ is a radical of one of the groups $M_1$ to $M_{145}$ and the radicals X, Q and M may be combined as desired.

$R^1$ and $R^2$ may be, for example, the following radicals:

| Compound No. | $R^1$ |
|---|---|
| $Q_1$ | H |
| $Q_2$ | F |
| $Q_3$ | Cl |
| $Q_4$ | Methyl |
| $Q_5$ | Ethyl |
| $Q_6$ | Propyl |
| $Q_7$ | 1-Methylethyl |
| $Q_8$ | Butyl |
| $Q_9$ | 1-Methylpropyl |
| $Q_{10}$ | 2-Methylpropyl |
| $Q_{11}$ | 1,1-Dimethylethyl |
| $Q_{12}$ | Pentyl |
| $Q_{13}$ | 1-Methylbutyl |
| $Q_{14}$ | 2-Methylbutyl |
| $Q_{15}$ | 3-Methylbutyl |
| $Q_{16}$ | 1,1-Dimethylpropyl |
| $Q_{17}$ | 1,2-Dimethylpropyl |
| $Q_{18}$ | 2,2-Dimethylpropyl |
| $Q_{19}$ | Cyclopropyl |
| $Q_{20}$ | Cyclobutyl |
| $Q_{21}$ | Cyclopentyl |
| $Q_{22}$ | Cyclohexyl |
| $Q_{23}$ | Cycloheptyl |
| $Q_{24}$ | Cyclooctyl |
| $Q_{25}$ | 1-Methylcyclopropyl |
| $Q_{26}$ | Cyclopropylmethyl |
| $Q_{27}$ | 1-(Cyclopropyl)ethyl |
| $Q_{28}$ | Chloromethyl |
| $Q_{29}$ | Dichloromethyl |
| $Q_{30}$ | Trichloromethyl |
| $Q_{31}$ | Chlorodifluoromethyl |
| $Q_{32}$ | Trifluoromethyl |
| $Q_{33}$ | Pentafluoroethyl |
| $Q_{34}$ | Difluoromethyl |
| $Q_{35}$ | 1-Chloroethyl |
| $Q_{36}$ | 2-Chloroethyl |
| $Q_{37}$ | 1-Methyl-1-chloroethyl |
| $Q_{38}$ | 1-Methyl-2-chloroethyl |
| $Q_{39}$ | Methoxymethyl |
| $Q_{40}$ | 1-Methylmethoxymethyl |
| $Q_{41}$ | 1-Methyl-2-methoxyethyl |
| $Q_{42}$ | 1-Methylethoxymethyl |
| $Q_{43}$ | Ethoxymethyl |
| $Q_{44}$ | Ethenyl |
| $Q_{45}$ | 1-Propenyl |
| $Q_{46}$ | 2-Propenyl |
| $Q_{47}$ | 1-Methylethenyl |
| $Q_{48}$ | 1-Ethylethenyl |
| $Q_{49}$ | 2-Phenylethenyl |
| $Q_{50}$ | 1-Butenyl |
| $Q_{51}$ | 2-Butenyl |
| $Q_{52}$ | 3-Butenyl |
| $Q_{53}$ | 1-Methyl-1-propenyl |
| $Q_{54}$ | 1-Methyl-2-propenyl |
| $Q_{55}$ | 2-Methyl-2-propenyl |
| $Q_{56}$ | 2-Propynyl |
| $Q_{57}$ | Methoxy |
| $Q_{58}$ | Ethoxy |
| $Q_{59}$ | Propoxy |
| $Q_{60}$ | 1-Methylethoxy |
| $Q_{61}$ | Butoxy |
| $Q_{62}$ | 1-Methylpropoxy |
| $Q_{63}$ | 1,1-Dimethylethoxy |
| $Q_{64}$ | Methylthio |
| $Q_{65}$ | Ethylthio |
| $Q_{66}$ | Chlorodifluoromethoxy |
| $Q_{67}$ | Trifluoromethoxy |
| $Q_{68}$ | Trichloromethylthio |
| $Q_{69}$ | Phenyl |
| $Q_{70}$ | 2-Fluorophenyl |
| $Q_{71}$ | 3-Fluorophenyl |
| $Q_{72}$ | 4-Fluorophenyl |
| $Q_{73}$ | 2-Chlorophenyl |
| $Q_{74}$ | 3-Chlorophenyl |
| $Q_{75}$ | 4-Chlorophenyl |
| $Q_{76}$ | 2-Methylphenyl |
| $Q_{77}$ | 3-Methylphenyl |
| $Q_{78}$ | 4-Methylphenyl |
| $Q_{79}$ | 2-Trifluoromethylphenyl |
| $Q_{80}$ | 3-Trifluorophenyl |
| $Q_{81}$ | 4-Trifluorophenyl |
| $Q_{82}$ | 2-Methoxyphenyl |
| $Q_{83}$ | 3-Methoxyphenyl |
| $Q_{84}$ | 4-Methoxyphenyl |
| $Q_{85}$ | 2,4-Dichlorophenyl |
| $Q_{86}$ | 2,4,6-Trimethylphenyl |
| $Q_{87}$ | Phenoxy |
| $Q_{88}$ | Phenylthio |
| $Q_{89}$ | 2-Chlorophenoxy |
| $Q_{90}$ | 3-Chlorophenoxy |
| $Q_{91}$ | 4-Chlorophenoxy |
| $Q_{92}$ | 2,4-Dichlorophenoxy |
| $Q_{93}$ | Benzyl |
| $Q_{94}$ | 2-Chlorobenzyl |
| $Q_{95}$ | 3-Chlorobenzyl |
| $Q_{96}$ | 4-Chlorobenzyl |
| $Q_{97}$ | 2-Fluorobenzyl |
| $Q_{98}$ | 3-Fluorobenzyl |
| $Q_{99}$ | 4-Fluorobenzyl |
| $Q_{100}$ | 2-Thienyl |
| $Q_{101}$ | 3-Thienyl |
| $Q_{102}$ | 2-Pyridyl |
| $Q_{103}$ | 3-Pyridyl |
| $Q_{104}$ | 4-Pyridyl |

Com-

-continued

| Compound No. | R² |
|---|---|
| M₁ | Methyl |
| M₂ | Ethyl |
| M₃ | Propyl |
| M₄ | 1-Methylethyl |
| M₅ | Butyl |
| M₆ | 1-Methylpropyl |
| M₇ | 2-Methylpropyl |
| M₈ | 1,1-Dimethylethyl |
| M₉ | Pentyl |
| M₁₀ | 1-Methylbutyl |
| M₁₁ | 2-Methylbutyl |
| M₁₂ | 3-Methylbutyl |
| M₁₃ | 1,1-Dimethylpropyl |
| M₁₄ | 1,2-Dimethylpropyl |
| M₁₅ | 2,2-Dimethylpropyl |
| M₁₆ | 1-Ethylpropyl |
| M₁₇ | Hexyl |
| M₁₈ | 1-Methylpentyl |
| M₁₉ | 2-Methylpentyl |
| M₂₀ | 3-Methylpentyl |
| M₂₁ | 4-Methylpentyl |
| M₂₂ | 1,1-Dimethylbutyl |
| M₂₃ | 1,2-Dimethylbutyl |
| M₂₄ | 1,3-Dimethylbutyl |
| M₂₅ | 2,2-Dimethylbutyl |
| M₂₆ | 2,3-Dimethylbutyl |
| M₂₇ | 3,3-Dimethylbutyl |
| M₂₈ | 1-Ethylbutyl |
| M₂₉ | 2-Ethylbutyl |
| M₃₀ | 1,1,2-Trimethylpropyl |
| M₃₁ | 1,2,2-Trimethylpropyl |
| M₃₂ | 1-Ethyl-1-methylpropyl |
| M₃₃ | 1-Ethyl-2-methylpropyl |
| M₃₄ | Cyclopropyl |
| M₃₅ | Cyclobutyl |
| M₃₆ | Cyclopentyl |
| M₃₇ | Cyclohexyl |
| M₃₈ | Cycloheptyl |
| M₃₉ | Cyclooctyl |
| M₄₀ | 1-Methylcyclopropyl |
| M₄₁ | Cyclopropylmethyl |
| M₄₂ | 1-(Cyclopropyl)ethyl |
| M₄₃ | 1-Methylcyclohexyl |
| M₄₄ | 1-Ethylcyclohexyl |
| M₄₅ | Cyclohexylmethyl |
| M₄₆ | 2-Propenyl |
| M₄₇ | 1-Methyl-2-propenyl |
| M₄₈ | 1,1-Dimethyl-2-propenyl |
| M₄₉ | 2-Propynyl |
| M₅₀ | 1-Methyl-2-propynyl |
| M₅₁ | 1,1-Dimethylpropynyl |
| M₅₂ | Phenylmethyl |
| M₅₃ | 1-Methylphenylmethyl |
| M₅₄ | 1,1-Dimethylphenylmethyl |
| M₅₅ | 2-Phenylethyl |
| M₅₆ | 2-Methylthioethyl |
| M₅₇ | 1-Methyl-2-methylthioethyl |
| M₅₈ | 1,1-Dimethyl-2-methylthioethyl |
| M₅₉ | 3-Methylthiopropyl |
| M₆₀ | 2-Fluoroethyl |
| M₆₁ | 2-Fluoro-1-methylethyl |
| M₆₂ | 1,1-Dimethyl-2-fluoroethyl |
| M₆₃ | 2-Chloroethyl |
| M₆₄ | 2-Chloro-1-methylethyl |
| M₆₅ | 2-Chloro-1,1,-dimethylethyl |
| M₆₆ | 2-Methyoxyethyl |
| M₆₇ | 2-Methoxy-1-methylethyl |
| M₆₈ | 1,1-Dimethyl-2-methoxyethyl |
| M₆₉ | 3-Methoxypropyl |
| M₇₀ | 2-Cyanoethyl |
| M₇₁ | 2-Cyano-1-methylethyl |
| M₇₂ | 2-Cyano-1,1-dimethylethyl |
| M₇₃ | Dimethylamino |
| M₇₄ | Diethylamino |
| M₇₅ | Morpholino |
| M₇₆ | Piperidino |
| M₇₇ | Phenyl |
| M₇₈ | 2-Methylphenyl |
| M₇₉ | 3-Methylphenyl |
| M₈₀ | 4-Methylphenyl |
| M₈₁ | 2-Ethylphenyl |
| M₈₂ | 3-Ethylphenyl |
| M₈₃ | 4-Ethylphenyl |
| M₈₄ | 2,3-Dimethylphenyl |
| M₈₅ | 2,4-Dimethylphenyl |
| M₈₆ | 2,5-Dimethylphenyl |
| M₈₇ | 2,6-Dimethylphenyl |
| M₈₈ | 3,4-Dimethylphenyl |
| M₈₉ | 3,5-Dimethylphenyl |
| M₉₀ | 2,3,4-Trimethylphenyl |
| M₉₁ | 2,3,5-Trimethylphenyl |
| M₉₂ | 2,4,5-Trimethylphenyl |
| M₉₃ | 2,4,6-Trimethylphenyl |
| M₉₄ | 3,4,5-Trimethylphenyl |
| M₉₅ | 2-Trifluoromethylphenyl |
| M₉₆ | 3-Trifluoromethylphenyl |
| M₉₇ | 4-Trifluoromethylphenyl |
| M₉₈ | 2-Fluorophenyl |
| M₉₉ | 3-Fluorophenyl |
| M₈₈ | 3,4-Dimethylpheny |
| M₈₉ | 3,5-Dimethylphenyl |
| M₉₀ | 2,3,4-Trimethylphenyl |
| M₉₁ | 2,3,5-Trimethylphenyl |
| M₉₂ | 2,4,5-Trimethylphenyl |
| M₉₃ | 2,4,6-Trimethylphenyl |
| M₉₄ | 3,4,5-Trimethylphenyl |
| M₉₅ | 2-Trifluoromethylphenyl |
| M₉₆ | 3-Trifluoromethylphenyl |
| M₉₇ | 4-Trifluoromethylphenyl |
| M₉₈ | 2-Fluorophenyl |
| M₉₉ | 3-Fluorophenyl |
| M₁₀₀ | 4-Fluorophenyl |
| M₁₀₁ | 2-Chlorophenyl |
| M₁₀₂ | 3-Chlorophenyl |
| M₁₀₃ | 4-Chlorophenyl |
| M₁₀₄ | 2,3-Difluorophenyl |
| M₁₀₅ | 2,4-Difluorophenyl |
| M₁₀₆ | 2,5-Difluorophenyl |
| M₁₀₇ | 2,6-Difluorophenyl |
| M₁₀₈ | 2,3-Dichlorophenyl |
| M₁₀₉ | 2,4-Dichlorophenyl |
| M₁₁₀ | 2,5-Dichlorophenyl |
| M₁₁₁ | 2,6-Dichlorophenyl |
| M₁₁₂ | 2,3,4-Trichlorophenyl |
| M₁₁₃ | 2,3,5-Trichlorophenyl |
| M₁₁₄ | 2,4,6-Trichlorophenyl |
| M₁₁₅ | 3,4,5-Trichlorophenyl |
| M₁₁₆ | 2-Cyanophenyl |
| M₁₁₇ | 3-Cyanophenyl |
| M₁₁₈ | 4-Cyanophenyl |
| M₁₁₉ | 2-Methoxyphenyl |
| M₁₂₀ | 3-Methoxyphenyl |
| M₁₂₁ | 4-Methoxyphenyl |
| M₁₂₂ | 2,3-Dimethoxyphenyl |
| M₁₂₃ | 2,4-Dimethoxyphenyl |
| M₁₂₄ | 2,5-Dimethoxyphenyl |
| M₁₂₅ | 2,6-Dimethoxyphenyl |
| M₁₂₆ | 3,4-Dimethoxyphenyl |
| M₁₂₇ | 3,5-Dimethoxyphenyl |
| M₁₂₈ | 3,4,5-Trimethoxyphenyl |
| M₁₂₉ | 2-Trifluoromethoxyphenyl |
| M₁₃₀ | 3-Trifluoromethoxyphenyl |
| M₁₃₁ | 4-Trifluoromethoxyphenyl |
| M₁₃₂ | 2-Nitrophenyl |
| M₁₃₃ | 3-Nitrophenyl |
| M₁₃₄ | 4-Nitrophenyl |
| M₁₃₅ | 2,3-Dinitrophenyl |
| M₁₃₆ | 2,4-Dinitrophenyl |
| M₁₃₇ | 2,5-Dinitrophenyl |
| M₁₃₈ | 2,6-Dinitrophenyl |
| M₁₃₉ | 3,4-Dinitrophenyl |
| M₁₄₀ | 3,5-Dinitrophenyl |
| M₁₄₁ | 1-Naphthyl |
| M₁₄₂ | 2-Naphthyl |
| M₁₄₃ | 3-Tetrahydrofuryl |
| M₁₄₄ | 4-Tetrahydropyranyl |
| M₁₄₅ | 2-Thiazolyl |

TABLE 1

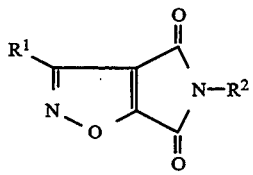

| Example no. | R¹ | R² | Physical data mp. [°C.], ¹H-NMR (250 MHZ, CDCl₃) [δ in ppm] |
|---|---|---|---|
| 1.001 | Methyl | tert.-Butyl | 48–50 |
| 1.002 | Ethyl | cyclo-Propyl | 58–60 |
| 1.003 | iso-Propyl | tert.-Butyl | 60–62 |
| 1.004 | n-Propyl | tert.-Butyl | 1.00(t; 3H), 1.63(s; 9H), 1.84(m; 2H), 2.76(t; 2H) |
| 1.005 | cyclo-Propyl | tert.-Butyl | 35–38 |
| 1.006 | iso-Propyl | cyclo-Propyl | 0.82–1.10 (m; 4H), 3.24(sept; 1H) |
| 1.007 | CH₂=C(C₂H₅)— | cyclo-Propyl | 95–96 |
| 1.008 | CH₃—CH(Cl)— | cyclo-Propyl | 0.90–1.08(m; 4H), 1.97(d; 3H), 2.62(m; 1H), 5.20(q; 1H) |
| 1.009 | cyclo-Propyl | cyclo-Propyl | 89–90 |
| 1.010 | iso-Propyl | 4-chlorophenyl | 80–82 |

TABLE 2

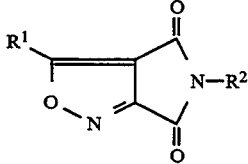

| Example no. | R¹ | R² | Physical data mp. [°C.], ¹H-NMR (250 MHZ, CDCl₃) [δ in ppm] |
|---|---|---|---|
| 2.001 | Methyl | tert.-Butyl | 48–50 |
| 2.002 | n-Propyl | tert.-Butyl | 48–49 |
| 2.003 | iso-Propyl | tert.-Butyl | 35–36 |
| 2.004 | cyclo-Propyl | cyclo-Propyl-methyl | 42–46 |
| 2.005 | cyclo-Propyl | Benzyl | 72–77 |
| 2.006 | cyclo-Propyl | —CH₂—CH₂—O—CH₃ | 1.00–1.45(m; 4H); 2.32(m; 1H), 3.34(s; 3H), 3.60(t; 2H) 3.84(t; 2H) |
| 2.007 | Methyl | cyclo-Butyl | 55–60 |
| 2.008 | Methyl | —C(CH₃)₂—C₂H₅ | 0.86(t; 3H), 1.63(s; 6H), 1.97(q; 2H), 2.66(s; 3H) |
| 2.009 | Methyl | —CH₂—C(CH₃)₃ | 84–91 |
| 2.010 | Methyl | sec.-Butyl | 0.88(t; 3H), 1.34(d; 3H) 1.65–2.10(m; 2H) 2.68(s; 3H) 4.20(m; 1H) |
| 2.011 | Methyl | cyclo-Pentyl | 71–78 |
| 2.012 | iso-Propyl | cyclo-Propyl | 70–73 |

TABLE 3

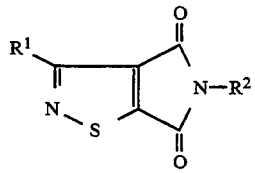

| Example no. | R¹ | R² | Physical data mp. [°C.] |
|---|---|---|---|
| 3.001 | iso-Propyl | tert.-Butyl | 52–53 |
| 3.002 | iso-Propyl | 4-Cl-Phenyl | 99–100 |
| 3.003 | Ethyl | 4-Cl-Phenyl | 121–123 |
| 3.004 | Phenyl | 4-Cl-Phenyl | 146–147 |

2. Preparation of precursors for the compounds Ic.
4(5)-tert-Butylaminocarbonyl-2-methylthiazole-5(4)-carboxylic acid 4(5)-Ethoxycarbonyl-2-methylthiazole-5(4)-carboxylic acid A solution of 8.5 g (0.213 mol) of sodium hydroxide in 100 ml of water were added dropwise to a solution of 51.8 g (0.213 mol) of diethyl 2-methylthiazole-4,5-dicarboxylate in 300 ml of ethanol at 0° C. The mixture was stirred for 12 hours at room temperature, after which the solvent was removed under reduced pressure, the residue was taken up in 100 ml of ether and 200 ml of water, the phases were separated and the aqueous phase was acidified to pH 1 with concentrated HCl. The product obtained in the form of an oil was isolated by extraction with CH₂Cl₂. Yield: 34.8 g (76%) as a 3:2 isomer mixture.

4-Ethoxycarbonyl-2-methylthiazole-5-carboxylic acid (main component)

¹H-NMR (CDCl₃, 250 MHz) δ=1.50 (t, I=7 Hz; 3 H), 2.80 (s; 3 H), 4.62 (q, I=7 Hz; 2 H), 13.50 (s, 1 H).

5-Ethoxycarbonyl-2-methylthiazole-5-carboxylic acid (secondary component)

¹H-NMR (CDCl₃, 250 MHz) δ=1.52 (t, I=7 Hz; 3 H), 2.82 (s; 3 H), 4.53 (q, 2 H), 13.50 (s, 1 H).

Ethyl 4(5)-tert-butylaminocarbonyl-2-methyl-thiazole-5(4)-carboxylate 3.20 g (40.9 mmol) of pyridine were added to a solution of 8 g (37.2 mmol) of 4(5)-ethoxycarbonyl-2-methylthiazole-5(4)-carboxylic acid in 50 mol of toluene. Stirring was carried out for 30 minutes, after which 4.70 g (39.8 mmol) of thionyl chloride were added dropwise. The mixture obtained was stirred for 2 hours at 60° C. and then cooled to 0° C. and 8 g (110 mmol) of tert-butylamine were added. Stirring was continued for 12 hours at room temperature, the solvent was removed under reduced pressure and the residue was taken up with 100 ml of ether and 50 ml of water. The solution was extracted again with 100 ml of ether, the combined extracts were dried and the solvent was removed. 9.70 g (97%) of product remained as a residue in the form of a crystal slurry (3:2 isomer mixture).

Ethyl 5-tert-butylaminocarbonyl-2-methylthiazole-4-carboxylate (main component)

¹H-NMR (CDCl₃, 250 MHz) δ=1.45 (t, 3 H), 1.45 (s; 3 H), 2.71 (s; 3 H), 4.50 (q, I=7 Hz; 2 H), 9.95 (s, 1 H).

Ethyl 4-tert-butylaminocarbonyl-2-methylthiazole-5-carboxylate (secondary component)

¹H-NMR (CDCl₃, 250 MHz) δ=1.37 (t, 3 H), 1.45 (s; 9 H), 2.71 (s; 3 H), 4.38 (q, 2 H), 7.84 (s; 1 H).

4(5)-tert-Butylaminocarbonyl-2-methylthiazole-5(4)-carboxylic acid 1.70 g (43.1 mmol) of sodium hydroxide in 20 ml of water were added to a solution of 9.70 g (35.9 mmol) of ethyl 4(5)-tert-butylaminocarbonyl-2-methylthiazole-5(4)-carboxylate in 100 ml of ethanol. The mixture was refluxed for two hours, the solvent was then removed under reduced pressure and the residue was taken up with 100 ml of water and 50 ml of ether. The phases were separated, the aqueous phase was brought to pH 1 with 10% strength hydrochloric acid and the precipitated produce (3:2 isomer mixture) was filtered off under suction and dried. Yield: 6.60 g (74%), mp.: 125°–129° C.

5-tert-Butylaminocarbonyl-2-methylthiazole-4-carboxylic acid (main component)

$^1$H-NMR (CDCl$_3$, 250 MHz) $\delta = 1.45$ (s, 9 H), 2.68 (s; 3 H), 8.00 (s, 1 H), 16.75 (s, 1 H).

4-tert-Butylaminocarbonyl-2-methylthiazole-5-carboxylic acid (secondary component)

$^1$H-NMR (CDCl$_3$, 250 MHz) $\delta = 1.52$ (s, 9 H), 2.73 (s; 3 H), 10.00 (s, 1 H), 16.75 (s, 1 H).

4-Cyclopropylaminocarbonyl-2-(1-methylethyl)-oxazole-5-carboxylic acid 0.12 mol of n-butyllithium (80.0 ml of a 1.5 molar solution in hexane) was added dropwise to a solution of 10.4 g (0.054 mol) of 2-(1-methylethyl)-oxazole-4-carboxylic acid cyclopropylamide in 250 ml of tetrahydrofuran under a nitrogen atmosphere of −70° C. and stirring was carried out for 30 minutes at this temperature. Thereafter, the reaction mixture was poured onto 500 g of solid CO$_2$ and was left to stand overnight. The mixture was evaporated down, the residue was taken up in 200 ml of water and 30 ml of 10% strength NaOH, the solution was extracted twice with diethyl ether and the aqueous phase was acidified to pH 2 with concentrated hydrochloric acid and extracted with ethyl acetate. The organic phase was dried with magnesium sulfate and the solvent was stripped off under reduced pressure. 10.4 g (81%) of 4-cyclopropylaminocarbonyl-2-(1-methylethyl)-oxazole-5-carboxylic acid were obtained as a white powder of melting point 109°–112° C.

4-tert-Butylaminocarbonyl-2-methoxythiazole-5-carboxylic acid 65 ml of a 1.5M solution (97 mmol) of n-butyllithium in n-hexane were added dropwise to a solution of 8.00 g (37 mmol) of 2-methoxythiazole-4-carboxylic acid tert-butylamide in 150 ml of tetrahydrofuran at −70° C. and the mixture was stirred for 30 minutes at this temperature. Thereafter, the reaction mixture was poured onto 500 g of solid carbon dioxide and allowed to warm up to room temperature in the course of 14 hours. The solvent was removed under reduced pressure, the residue was taken up in a mixture of 150 ml of water and 16 ml of 2M sodium hydroxide solution, the solution was filtered, the filtrate was acidified with concentrated hydrochloric acid and the precipitated carboxylic acid was filtered off under suction.

7.80 g (82%) of 4-tert-butylaminocarbonyl-2-methoxythiazole-5-carboxylic acid were obtained as a white power of melting point 120°–122° C.

3. Preparation of the oxazole- or thiazole-4,5-dicarboximides Ic

N-tert-Butyl-2-methylthiazole-4,5-dicarboximide 6.60 g(27.3 mmol) of 4(5)-tert-butylaminocarbonyl-2-methylthiazole-5(4)-carboxylic acid were dissolved in 20 ml of pyridine, 6.20 g (32.7 mmol) of p-toluenesulfonyl chloride were added and the mixture was stirred for 12 hours at room temperature. The solvent was removed under reduced pressure, the residue was taken up with CH$_2$Cl$_2$ and water, the phases were separated and the organic phase was washed in succession with 10% strength HCl, saturated NaHCO$_3$ solution and water and dried. The residue which remained after removal of the solvent was purified by filtration over silica gel (eluant: CH$_2$Cl$_2$). Yield: 5.20 g (85%), mp.: 106° C. (Active ingredient Example No. 4.013).

$^1$H-NMR (CDCl$_3$, 250 MHz) $\delta = 1.65$ (s, 9 H), 2.89 (s; 3 H).

N-(3-Trifluoromethylphenyl)-2-(1-methylethyl)-thiazole-4,5-dicarboximide 11.5 g (37 mmol) of 4(5)-(3-trifluoromethylanilino)-carbonyl-2-(1-methylethyl)-thiazole-5(4)-carboxylic acid were dissolved in 100 ml of pyridine, and 8.5 g (44.5 mmol) of p-toluenesulfonyl chloride were added at 0° C. The mixture was allowed to warm up to room temperature and was then heated at 60° C. for two hours. The solvent was removed under reduced pressure, the residue was taken up in CH$_2$Cl$_2$ and water, the phases were separated, the aqueous phase was extracted once again with CH$_2$Cl$_2$ and the combined extracts were washed in succession with 10% strength HCl, saturated NaHCO$_3$ solution and water. The organic phase was dried over NA$_2$SO$_4$, the mixture was evaporated down and the remaining residue was purified by filtration over silica gel (eluant: CH$_2$Cl$_2$). Yield: 10.65 g (84%) of a product of melting point 80° C. (Active ingredient Example No. 4.015).

$^1$H-NMR (CDCl$_3$, 250 MHz) $\delta = 1.52$ (d, 6 H), 3.50 (sept.; 1 H), 7.55–7.75 (m; 3 H).

N-tert-Butyl-2-methoxythiazole-4,5-dicarboximide 3.75 g (37.1 mmol) of N-methylmorpholine, 1.20 g (10 mmol) of 4-N,N-dimethylaminopyridine and 8.70 g of a 50% strength solution (13.7 mmol) of propanephosphonic anhydride in CH$_2$Cl$_2$ were added in succession to a solution of 2.6 g (10 mmol) of 4-tert-butylaminocarbonyl-2-methoxythiazole-5-carboxylic acid in 100 ml of CH$_2$Cl$_2$ at −5° C. The mixture was refluxed for 6 hours, after which the solvent was removed and the residue was taken up with ethyl acetate. The solution was extracted twice with saturated sodium bicarbonate solution and once with 5% strength citric acid solution, washed with water and dried over MgSO$_4$. After removed of the solvent, the crude product was purified by chromatography over silica gel (eluant: 1:1 cyclohexane/ethyl acetate) and 1.20 g (50%) of product of melting point 63°–66° C. were obtained in this manner (Active ingredient Example No. 4.014)

The compounds listed in Table 4 below were prepared similarly to the above Examples:

TABLE 4

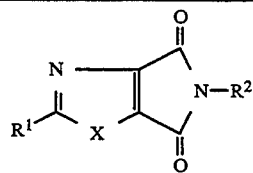

| No. | R¹ | R² | | mp (°C.) or ¹H-NMR (CDCl₃, 250 MHZ) |
|---|---|---|---|---|
| 4.001 | Benzyl | 1,1-Dimethylethyl | S | 72–74 |
| 4.002 | 1-Phenylethyl | 1,1-Dimethylethyl | S | 1.61(s; 9H), 1.82(d; 3H), 4.54(q; 1H), 7.24–7.42(m; 5H) |
| 4.003 | cyclo-Propyl | 1,1-Dimethylethyl | S | 84 |
| 4.004 | 1-Methoxymethyl | 1,1-Dimethylethyl | S | 51–52 |
| 4.005 | 1,1-Dimethylethyl | 1,1-Dimethylethyl | S | 116 |
| 4.006 | 4-Fluorbenzyl | 1,1-Dimethylethyl | S | 92 |
| 4.007 | 3,4,5-Trimethoxybenzyl | 1,1-Dimethylethyl | S | 123 |
| 4.008 | 2-Phenylethyl | 1,1-Dimethylethyl | S | 83–84 |
| 4.009 | Phenyl | 1,1-Dimethylethyl | S | 115 |
| 4.010 | 1-Methylethyl | 1,1-Dimethylethyl | S | 86 |
| 4.011 | H | 1,1-Dimethylethyl | S | 90–91 |
| 4.012 | 4-Phenoxyphenyl | 1,1-Dimethylethyl | S | 141–143 |
| 4.013 | Methyl | 1,1-Dimethylethyl | S | 105–107 |
| 4.014 | Methoxy | 1,1-Dimethylethyl | S | 63–66 |
| 4.015 | 1-Methylethyl | 3-Trifluormethylphenyl | S | 80 |
| 4.016 | Methyl | 3-Trifluormethylphenyl | S | 2.95(s; 3H), 7.55–7.75(m; 4H). |
| 4.017 | Methyl | 4-Phenylphenyl | S | >250 |
| 4.018 | 2-Methylpropyl | 1,1-Dimethylethyl | S | 1.00(d; 6H), 2.20(nonett; 1H), 1.66(s; 9H), 3.00(d; 2H). |
| 4.019 | 1-Methylethyl | Methoxy | S | 70 |
| 4.020 | Methylthiomethyl | 1,1-Dimethylethyl | S | 1.65(s; 9H), 2.20(s; 3H), 4.05(s; 2H). |
| 4.021 | Butyl | 1,1-Dimethylethyl | S | 0.95(t; 3H), 1.45(m; 2H), 1.65(s; 9H), 1.85(sext; 2H), 3.15(t; 2H). |
| 4.022 | Methyl | Methyl | S | 97–99 |
| 4.023 | Methyl | Cyclopropyl | S | 111 |
| 4.024 | Methyl | 1-Methylethyl | S | 80–81 |
| 4.025 | Propyl | 1,1-Dimethylethyl | S | 42–44 |
| 4.026 | 2-Pyridyl | 1,1-Dimethylethyl | S | 129 |
| 4.027 | Methylsulfonylmethyl | 1,1-Dimethylethyl | S | 113–115 |
| 4.028 | Methyl | 1-Methyl-2-thiomethylpropyl | S | 1.75(s; 6H), 210(s; 3H), 2.90(s; 3H), 3.15(s; 2H) |
| 4.029 | Methyl | 2,2,2-Trifluoromethylphenyl | | 147 |
| 4.030 | Methyl | 2-Methoxy-1-methylethyl | S | 1.40(d; 3H), 2,90(s; 3H), 3.30(s; 3H) 3.50 and 3.90(ABX System; 2H), 4.40–4.60(m; 1H) |
| 4.031 | Methyl | 4-Chlorophenyl | S | 182 |
| 4.032 | Methyl | Dimethylamino | S | 48 |
| 4.033 | Methyl | 1,1-Dimethyl-2-propinyl | S | 46 |
| 4.034 | Methyl | Cyclopropyl | S | 43–44 |
| 4.035 | Methyl | Benzyl | S | 113 |
| 4.036 | Methyl | Cyclo-Propylmethyl | S | 56 |
| 4.037 | Methyl | 2-Propenyl | S | 86 |
| 4.038 | Methyl | 1-Phenylethyl | S | 91 |
| 4.039 | Methyl | 4-Chloro-3-(-2-chloro-4-trifluoromethyl-phenoxy)-phenyl | S | 2.95(s; 3H), 6.95–7.80(m, 6H) |
| 4.040 | Methyl | 4-Chloro-2-methyl-phenyl | S | 2.20(s; 3H), 2.90(s; 3H), 7.00–7.40(m; 3H) |
| 4.041 | Methyl | 2-Methyl-1-(2-propyl)-propyl | S | 0.95(d; 6H), 1.00(d; 6H), 2.40–2.60(m; 2H) 2.90(s; 3H), 3,70(t; 1H) |
| 4.042 | Methyl | 4-Phenyl-cyclohexyl | S | 179 |
| 4.043 | Cyclopropyl | Cyclopropyl | S | 100–101 |
| 4.044 | Methyl | 2-(iso-Propyl)-phenyl | S | 131–133 |
| 4.045 | Methyl | 4-Methoxy-phenyl | S | 210–212 |
| 4.046 | Methyl | 2,5-Dimethoxy-phenyl | S | 147–150 |
| 4.047 | Methyl | 2,4,6-Trimethylphenyl | S | 133–134 |
| 4.048 | Methyl | 3-Methoxyphenyl | S | 117–119 |
| 4.049 | Methyl | 2,4-Difluorophenyl | S | 152–154 |
| 4.050 | Methyl | 4-Trifluoromethylphenyl | S | 221–223 |
| 4.051 | Methyl | 3-Trifluoromethoxyphenyl | S | 107–109 |
| 4.052 | Methyl | 2-Benzothiazolyl | S | >220 |
| 4.053 | Methyl | Cyclohexylmethyl | S | 94 |
| 4.054 | Methyl | Cyclohexyl | S | 173 |
| 4.055 | Methyl | 2-(1,3,4-Thiadiazolyl) | S | 177–178 |
| 4.056 | Methyl | 1-Indanyl | S | 106–108 |
| 4.057 | Methyl | 3-Sulfolanyl | S | 197–198 |
| 4.058 | Methyl | 1,1,3,3-Tetramethyl-butyl | S | 1.00(s; 9H), 1.85(s; 6H), 2.00(s; 2H). 2.90(s; 3H) |
| 4.059 | Methyl | Adamantyl | S | 132–134 |
| 4.060 | Methyl | 4-Thiomethylphenyl | S | >250 |
| 4.061 | Methyl | 8-Chinolinyl | S | 207 |

TABLE 4-continued

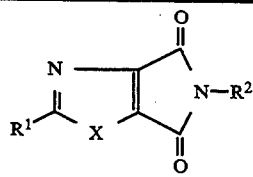

| No. | R[1] | R[2] | X | mp (°C.) or $^1$H-NMR (CDCl$_3$, 250 MHZ) |
|---|---|---|---|---|
| 4.062 | Methyl | 2-Cyano-1,1-dimethylethyl | S | 1.85(s; 6H), 2.90(s; 3H), 3.10(s; 2H). |
| 4.063 | Methyl | 3-Tetrahydrofuranyl | S | 73-75 |
| 4.64 | Methyl | 1-Cyano-1-methylethyl | S | 82 |
| 4.065 | Methyl | 2-(1,4-Benzoquinonyl) | S | 127 |
| 4.066 | Methyl | 3-Ethyl-pentyn-3-yl | S | 1.05(t; 6H), 1.95(m; 4H), 2.50(m; 4H), 2.60(s; 1H), 2.95(s; 3H) |
| 4.067 | Methyl | 1-tert-Butoxy-propan-2-yl | S | 1.10(s; 9H), 1.45(d; 3H), 2.90(s; 3H), 3.65(m; 1H), 3.80(dd; 1H), 4.40(m; 1H). |
| 4.068 | Methyl | 1-Cyclopropyl-ethyl | S | 0.15-0.85(m; 4H), 1.55(d; 3H), 1.55-1.65(m; 1H), 2.95(s; 3H), 3.25-3.50(m; 1H). |
| 4.069 | Methyl | 2,6-Dimethyl-undeca-2,6-dien-10-yl | S | 1.30-2.30(m; 20H), 2.90(s; 3H) 4.25(m; 1H), 5.05(m; 2H). |
| 4.070 | Methyl | 2-Methyl-4-phenyl-butan-2-yl | S | 1.70(s; 6H), 2.20-2.40(m; 2H) 2.50-2.70(m; 2H), 2.90(s; 3H), 6.95-7.25(m; 5H) |
| 4.071 | Methyl | Cyclododecanyl | S | 90-91 |
| 4.072 | Methyl | 2-Methyl-pentan-2-yl | S | 0.95(t; 3H), 1.65(s; 6H), 2.00(q; 2H), 2.85(s; 3H). |
| 4.073 | Methyl | 2-Heptanyl | S | 0.85(t; 3H), 1.15-1.35(m; 6H), 1.40(d; 3H), 1.55-1.75(m; 1H), 1.95-2.10(m; 1H), 2.90(s; 3H), 4.15-4.45(m; 1H) |
| 4.074 | Methyl | Diphenylmethyl | S | 152 |
| 4.075 | Methyl | 4-Chloro-3-trifluoromethyl-phenyl | S | 141 |
| 4.076 | Methyl | Bicyclo[3.3.0]octan-1-yl | S | 61 |
| 4.077 | Methyl | 3,4-3,4-Dichlorophenyl | S | 174-176 |
| 4.078 | Methyl | 4-Methyl-tetrahydropyrdn-4-yl | S | 125 |
| 4.079 | Methyl | 2-Methyl-4-oxo-pentan-2-yl | S | 1.75(s; 6H), 2.15(s; 3H), 2.90(s; 3H), 3.20(s; 2H). |
| 4.080 | Methyl | 1-Chloro-butan-2-yl | S | 0.95(t; 3H), 1.70-2.15(m; 2H), 2.95(s; 3H) 3.75 and 4.10(ABX-System; 2H), 4.50(m; 1H). |
| 4.081 | Methyl | Bicyclo[2.2.1]heptan-2-yl | S | 100 |
| 4.082 | Methyl | 6-Methyl-heptan-2-yl | S | 0.80(d; 3H), 0.85(d, 3H), 1.10-2.10(m; 7H), 1.45(d; 3H), 2.40(s; 3H), 4.25(m; 1H). |
| 4.083 | Methyl | 3-Methyl-butyn-2-yl | S | 78 |
| 4.084 | Methyl | 6-Methyl-hept-5-en-2-yl | S | 1.45(d, 3H), 1.55(s; 3H), 1.60(s; 3H), 1.65-180(m; 1H), 1.90-2.15(m; 3H), 2.90(s; 3H), 4.20-4.35(m; 1H), 5.00-5.15(m; 1H). |
| 4.085 | Methyl | 1,2-Diphenylethyl | S | 134 |
| 4.086 | Methyl | Phenoxy-propan-2-yl | S | 71 |
| 4.087 | Phenyl | 1,1-Dimethylethyl | O | 130-138 |

Use Examples

The herbicidal action of the dicarboximides of the formulae Ia, Ib and Ic could be demonstrated by greenhouse experiments:

The culture vessels used were plastic flower pots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly watered in order to promote germination and growth and then covered with transparent plastic covers until the plants had begun to grow. The cover ensures uniform germination of the test plants, unless this is adversely affected by the active ingredients.

For the postemergence treatment, the test plants were treated with the active ingredients suspended or emulsified in water when said plants had reached a height of growth of from 3 to 15 cm, depending on the form of growth. The application rate for the postemergence treatment was 1 and 2 kg/ha of active substance.

The plants were kept at 10°-25° C. or 20°-35° C., depending on the species. The test period extended over from 2 to 4 weeks. During this time, the plants were tended and the reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments in the case of Example compound 4.003 consisted of the following species:

| Botanical name | Common name |
|---|---|
| *Chenopodium album* | lambsquarters (goosefoot) |
| *Stellaria media* | chickweed |

| Botanical name | Common name |
| --- | --- |
| *Veronica* spp. | speedwell |

When 1.0 kg/ha of active substance is used in the postemergence method, undesirable broad-leaved plants can be very readily controlled with Example compound No. 4.003.

The plants used in the greenhouse experiments in the case of Example compound 1.001 comprise the following species:

| Botanical name | Common name |
| --- | --- |
| *Chenopodium album* | lambsquarters (goosefoot) |
| *Chysanthemum coronarium* | crown daisy |
| *Setaria italica* | foxtail millet |
| *Solanum nigrum* | black nightshade |

Undesirable broad-leaved plants can be very readily controlled with Example 1.001 when used at a rate of 2.0 kg/ha active substance by the postemergence method.

We claim:

1. A dicarboximide of the formula Ia, Ib or Ic

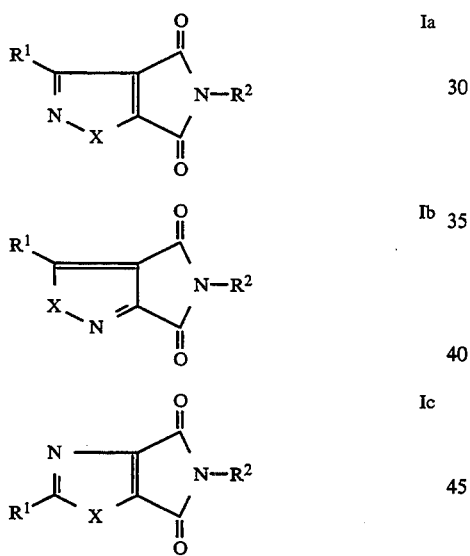

wherein X is oxygen;

$R^1$ is (a) hydrogen, (b) halogen, (c) cyano, (d) $C_1$-$C_6$-alkyl which may be substituted by 1-5 halogen atoms or one or two $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl or cyano groups, (e) $C_3$-$C_8$-cycloalkyl which may be substituted by 1-3 halogens or $C_1$-$C_4$-alkyl groups, (f) $C_2$-$C_6$-alkenyl which may be substituted by 1-3 halogen atoms, $C_1$-$C_3$-alkoxy or phenyl groups, wherein said phenyl groups may be substituted by one to three $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro groups (g) $C_2$-$C_6$-alkynyl which may be substituted by 1-3 halogen atoms, $C_1$-$C_3$-alkoxy or phenyl groups, wherein said phenyl groups may be substituted by one to three $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloal- kylthio, halogen, cyano or nitro groups, (h) $C_1$-$C_4$-alkoxy, (i) $C_2$-$C_6$-alkenyloxy, (j) $C_2$-$C_6$-alkynyloxy, (k) $C_1$-$C_4$-alkylthio, (l) $C_1$-$C_4$-haloalkoxy, (m) $C_1$-$C_4$-haloalkylthio, (n) $C_1$-$C_4$-alkylsulfonyl, (o) $C_1$-$C_4$-haloalkylsulfonyl, (p) phenoxy or phenylthio which may be substituted by one to three $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro groups, (q) a 5-membered or 6-membered saturated or aromatic heterocyclic group containing one or two heteroatoms selected from the group consisting of oxygen, sulfur and nitrogen, which may be substituted by one or two $C_1$-$C_3$-alkyl, halogen, $C_1$-$C_3$-alkoxy or $C_1$-$C_3$-alkoxycarbonyl groups, (r) a fused aromatic group selected from the group consisting of benzofuran-2-yl, benzofuran-3-yl, isobenzofuran-2-yl, benzothiophen-2-yl, benzothiophen-3-yl, isobenzothiophen-2-yl, indol-2-yl, indol-3-yl, 1,2-benzoisoxal-3-yl, benzoxal-2-yl, 1,2-benzoisothiazol-3-yl, benzothiazol-2-yl, indazol-3-yl, (1H)-benzimidazol-2-yl, quinol-3-yl, quinol-5-yl, quinol-6-yl, quinol-8-yl, isoquinol-1-yl and isoquinol-5-yl, which may be substituted by one or two $C_1$-$C_3$-alkyl, halogen, $C_1$-$C_3$-alkoxy or $C_1$-$C_3$-alkoxycarbonyl groups, (s) phenyl or phenyl-$C_1$-$C_4$alkyl which may be substituted by one to three $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, halogen, nitro or cyano groups;

$R^2$ is (t) hydrogen, (u) hydroxyl, (v) $C_1$-$C_4$-alkoxy, (w) $C_1$-$C_6$-alkyl which may be substituted by 1-3 cyano, $C_1$-$C_4$-alkoxy-$C_1$-$C_4$-alkoxy, $C_1$-$C_4$-alkoxy, $C_1$-$C_4$-haloalkoxy, $C_1$-$C_4$-alkylthio, $C_1$-$C_4$-haloalkylthio, di-$C_1$-$C_4$-alkylamino, halogen, $C_3$-$C_8$-cycloalkyl or phenyl groups, wherein said phenyl groups may be substituted by one to three halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio groups, (x) $C_3$-$C_8$-cycloalkyl which may be substituted by one to three $C_1$-$C_6$-alkyl, $C_1$-$C_6$-haloalkyl, $C_1$-$C_4$-alkoxy, $C_1$-$C_4$-haloalkoxy, halogen, nitro or cyano groups, (y) $C_3$-$C_6$-alkenyl which may be substituted by 1-3 halogen atoms or one phenyl group, wherein said phenyl group may be substituted by one to three $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro groups (z) $C_3$-$C_6$-alkynyl which may be substituted by 1-3 halogen atoms or one phenyl group, wherein said phenyl group may be substituted by one to three $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro groups (aa) di-$C_1$-$C_4$-alkylamino, (bb) a 5-membered or 6-membered saturated or aromatic heterocyclic group containing one or two heteroatoms selected from the group consisting of oxygen, sulfur and nitrogen, which may be substituted by one or two $C_1$-$C_3$-alkyl, halogen, $C_1$-$C_3$-alkoxy or $C_1$-$C_3$-alkoxycarbonyl groups, (cc) a fused aromatic group selected from the group consisting of benzofuran-2-yl, benzofuran-3-yl, isobenzofuran-2-yl, benzothiophen-2-yl, benzothiophen-3-yl, isobenzothiophen-2-yl, indol-2-yl, indol-3-yl, 1,2-benzoisoxal-3-yl, benzoxal-2-yl, 1,2-benzoisothiazol- 3-yl, benzothiazol-2-yl, indazol-3-yl, (1H)-benzimidazol-2-yl, quinol-3-yl, quinol-5-yl, quinol-6-yl, quinol-8-yl, isoquinol-1-yl and isoquinol-5-yl, where said fused aromatic group may be monosubstituted to trisubstituted by $C_1$–$C_4$-alkyl or halogen, (dd) phenyl which may be substituted by one to four $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, phenyl, $C_1$–$C_4$-alkanoyl, $C_1$–$C_4$-haloalkanoyl or $C_1$–$C_4$-alkoxycarbonyl groups or (ee) naphthyl which may be substituted by 1–3 halogen atoms or $C_1$–$C_4$-alkyl groups; and plant tolerated salts thereof, except for 3-methylisoxazole-4,5-dicarboximide.

2. The dicarboximide of claim 1, wherein $R^1$ is $C_1$–$C_6$-alkyl which may be substituted with 1–5 halogen atoms.

3. The dicarboximide of claim 1, wherein $R^1$ is $C_1$–$C_6$-alkyl which may be substituted with one or two substituents selected from the group consisting of $C_3$–$C_6$-cycloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl and cyano.

4. The dicarboximide of claim 1, wherein $R^1$ is $C_3$–$C_8$-cycloalkyl which may be substituted with 1–3 substituents selected from the group consisting of $C_1$–$C_4$-alkyl and halogen.

5. The dicarboximide of claim 1, wherein $R^1$ is $C_2$–$C_6$-alkenyl which may be substituted with 1–3 substituents selected from the group consisting of halogen, $C_1$–$C_3$-alkoxy, unsubstituted and substituted phenyl.

6. The dicarboximide of claim 5, wherein said phenyl is substituted with 1–3 substituents selected from the group consisting of $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano and nitro.

7. The dicarboximide of claim 1, wherein $R^1$ is $C_2$–$C_6$-alkynyl which may be substituted with 1–3 substituents selected from the group consisting of halogen, $C_1$–$C_3$-alkoxy unsubstituted and substituted phenyl.

8. The dicarboximide of claim 7, wherein said phenyl is substituted with 1–3 substituents selected from the group consisting of $C_1$–$C_4$-alkyl, $C_1$–$C_4$-haloalkyl, $C_1$-alkoxy, $C_1$–$C_4$-haloalkoxy, $C_1$–$C_4$-alkylthio, $C_1$–$C_4$-haloalkylthio, halogen, cyano and nitro.

9. The dicarboximide of claim 1, wherein $R^1$ is phenoxy or phenylthio which may be substituted with 1–3 substituents selected from the group consisting of $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano and nitro.

10. The dicarboximide of claim 1, wherein $R^1$ is phenyl or phenyl-$C_1$–$C_4$-alkyl which may be substituted with 1–3 substituents selected from the group consisting of $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro and cyano.

11. The dicarboximide of claim 1, wherein $R^2$ is $C_1$–$C_6$-alkyl which may be substituted with 1–3 substituents selected from the group consisting of cyano, $C_1$–$C_4$-alkoxy-$C_1$–$C_4$-alkoxy, $C_1$–$C_4$-alkoxy, $C_1$–$C_4$-haloalkoxy, $C_1$–$C_4$-alkylthio, $C_1$–$C_4$-haloalkylthio, di-$C_1$–$C_{C4}$-alkylamino, halogen, $C_3$–$C_8$-cycloalkyl unsubstituted and substituted phenyl.

12. The dicarboximide of claim 11, wherein said phenyl is substituted with 1–3 substituents selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, and $C_1$–$C_4$-haloalkylthio.

13. The dicarboximide of claim 1, wherein $R^2$ is $C_3$–$C_8$-cycloalkyl which may be substituted with 1–3 substituents selected from the group consisting of $C_1$–$C_6$-alkyl, $C_1$–$C_6$-haloalkyl, $C_1$–$C_4$-alkoxy, $C_1$–$C_4$-haloalkoxy, halogen, nitro and cyano.

14. The dicarboximide of claim 1, wherein $R^2$ is $C_3$–$C_6$-alkenyl which may be substituted with 1–3 halogens.

15. The dicarboximide of claim 1, wherein $R^2$ is $C_3$–$C_6$-alkenyl which may be substituted with one unsubstituted or substituted phenyl.

16. The dicarboximide of claim 15, wherein said phenyl is substituted with 1–3 substituents selected from the group consisting of $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano and nitro.

17. The dicarboximide of claim 1, wherein $R^2$ is $C_3$–$C_6$-alkynyl which may be substituted with 1–3 halogens.

18. The dicarboximide of claim 1, wherein $R^2$ is $C_3$–$C_6$-alkynyl which may be substituted with one unsubstituted or substituted phenyl.

19. The dicarboximide of claim 18, wherein said phenyl is substituted with 1–3 substituents selected from the group consisting of $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano and nitro.

20. The dicarboximide of claim 1, wherein $R^2$ is naphthyl which may be substituted with 1–3 halogens or $C_1$–$C_4$-alkyl groups.

21. The dicarboximide of claim 1, wherein $R^1$ is said fused aromatic group and said fused aromatic group is substituted by methyl.

22. The dicarboximide of claim 1, wherein $R^1$ is said fused aromatic group and said fused aromatic group is substituted by fluorine or chlorine.

23. The dicarboximide of claim 1, wherein $R^1$ is said fused aromatic group and said fused aromatic group is substituted by methoxy or ethoxy.

24. The dicarboximide of claim 1, wherein $R^1$ is said fused aromatic group and said fused aromatic group is substituted by methoxycarbonyl or ethoxycarbonyl.

25. A herbicidal composition which comprises inert additives and the dicarboximide of claim 1.

26. A method for controlling undesirable plant growth, wherein the undesirable plants or the area to be kept free of undesirable plant growth are or is treated with a herbicidally effective amount of the dicarboximide of claim 1 or 3-methylisoxazole-4,5-dicarboximide.

* * * * *

UNITED STATES PATENT AND TRADEMARK OFFICE
CERTIFICATE OF CORRECTION

PATENT NO. : 5,378,680
DATED : January 3, 1995
INVENTOR(S) : Volker MAYWALD, et al.

It is certified that error appears in the above-indentified patent and that said Letters Patent is hereby corrected as shown below:

On the title page, Item [75], the fifth inventor's name is spelled incorrectly. It should read:

--Wolfgang Freund--

Signed and Sealed this

Eleventh Day of April, 1995

*Attest:*

BRUCE LEHMAN

*Attesting Officer*  *Commissioner of Patents and Trademarks*